US006869937B1

(12) United States Patent
Cases et al.

(10) Patent No.: US 6,869,937 B1
(45) Date of Patent: Mar. 22, 2005

(54) ACYL COA:CHOLESTEROL ACYLTRANSFERASE (ACAT-2)

(75) Inventors: Sylvaine Cases, San Francisco, CA (US); Robert V. Farese, Jr., San Francisco, CA (US); Sandra K. Erickson, San Francisco, CA (US); Sabine Novak, Munich (DE); Michel Accad, San Francisco, CA (US)

(73) Assignees: The Regents of the Universtiy of California, Oakland, CA (US); The United States of America as represented by the Department of Veteran Affairs, Washington, DC (US)

(*) Notice: Subject to any disclaimer, the term of this patent is extended or adjusted under 35 U.S.C. 154(b) by 428 days.

(21) Appl. No.: 09/605,166

(22) Filed: Jun. 27, 2000

(Under 37 CFR 1.47)

Related U.S. Application Data

(63) Continuation-in-part of application No. 09/328,857, filed on Jun. 8, 1999.
(60) Provisional application No. 60/090,354, filed on Jun. 23, 1998.

(51) Int. Cl.[7] .................. A01N 43/04; A61K 31/70; A61K 38/00; C12N 9/00; C12N 5/00
(52) U.S. Cl. .................. 514/44; 514/12; 536/23.1; 536/410; 536/23.2; 536/348; 536/23.5; 435/32; 435/377; 435/252.3; 435/193
(58) Field of Search ................ 536/410, 23.1, 536/23.2, 348, 23.5; 435/32, 377, 252.3, 193; 514/44, 12

(56) References Cited

U.S. PATENT DOCUMENTS

| 5,484,727 | A | | 1/1996 | Chang et al. |
| 5,834,283 | A | * | 11/1998 | Chang et al. |
| 5,968,749 | A | * | 10/1999 | Chang et al. |
| 6,100,077 | A | * | 8/2000 | Sturley et al. ............. 435/193 |
| 6,444,876 | B1 | * | 9/2002 | Lassner et al. ............ 800/281 |
| 6,579,974 | B1 | * | 6/2003 | Cases et al. ............... 536/23.1 |
| 2002/0170091 | A1 | * | 11/2002 | Lassner et al. ............ 800/281 |
| 2003/0059420 | A1 | * | 3/2003 | Grabowski et al. ........ 424/94.6 |
| 2003/0096772 | A1 | * | 5/2003 | Crooke et al. ............... 514/44 |

FOREIGN PATENT DOCUMENTS

| WO | WO 94/09126 | * | 4/1994 |
| WO | WO 97/45439 | | 12/1997 |
| WO | WO 99/67368 | * | 9/1999 |

OTHER PUBLICATIONS

Tanaka et al, J. Med. Chem. 41:2390–2410, 1998.*
Tanaka et al, Bioorganic & Medicinal Chem. Letters 8:81–86, 1998.*
Tanaka et al, Bioorganic & Medicinal Chemistry 6:15–30, 1998.*
Roth, DDT 3/1:19–25, 1998.*
Nicolosi et al Atherosclerosis 137:77–85, 1998.*
Dugar et al Bioorganic & Medicinal Chemistry 319:1231–1236, 1995.*
White et al, J. Med. Chem. 39:3908–3919, 1996.*
Buhman et al, BBA 1529:142–154, 2000.*
Krause et al. Arterioscler. Thromb. 14:598–604, 1994.*
Chang et al JBC 268/28:20747–752, 1993.*
Buhman et al, Nature Medicine 6/12:1341–1347, 2000.*
Accad et al, J. Clin. Invest. 105:711–719, 2000.*
Chang et al, JBC, 275/36:28083–92, 2000.*
Izem et al, Biochem. J. 329:81–89, 1998.*
Cases et al JBC 273/41: 26755–764, 1998.*
Meiner et al JBC, 273/2: 1064–1069, 1998.*
Davignon Diabete & Metabolisme(Paris) 21:139–146, 1995.*
Lee et al Bioorganic & Med. Chem. Letters 8:289–294, 1998.*
Matsuda, Medicinal Research Reviews 14/3:271–305, 1994.*
Matsuda et al, BBA, 1301:76–94, 1996.*
O'Brien et al, J. Med. Chem., 39:2354–66, 1996.*
Vaccaro et al, J. Med. Chem., 39:1704–1719, 1996.*
Wang et al Arterioscler. Thromb. Vasc. Biol., 16:809–814, 1996.*
Junquero et al. Biochemical Pharmacology 61:387–398, 2001.*
Burnett et al, Clinica Chimica Acta, 286:231–42, 1999.*
Tanaka et al, J. Med. Chem. 41:4408–20, 1998.*
Sellers et al, Toxicol. Sci. 46:151–154, 1998.*
Rudel et al, Current Opinion in Lipidology 12:121–127, 2001.*
Rudel et al Nature Medicine 6/12:1313–14, 2000.*
Cao et al, JBC, 271/24:14642–48, 1996.*
Khelef et al, JBC, 273/18:11218–224, 1998.*
Fazio et al J. Clinical Invest. 107/2:163–71, 2001.*
Yang et al, JBC, 276/24:20989–998, 2001.*
Seo et al, Circulation vol. 100, No. 18 Abstract #3228 Suppl I pI–612, 1999.*
Becker et al, Arterioscler. Thromb. 14:1346–1355, 1994.*
Pape et al, J. Lipid Research 36:823–38, 1995.*
Sonda et al JBC, 276/37:34434–440, 2001.*
Sturley, Current Opinion in Lipdology, 1997, 8:167–173.*

(List continued on next page.)

*Primary Examiner*—Nita Minnifield
(74) *Attorney, Agent, or Firm*—Paula A. Borden; Bret E. Field; Bozicevic, Field & Francis, LLP

(57) ABSTRACT

Nucleic acid compositions encoding novel ACAT proteins, as well as the novel ACAT-2 proteins, (ACAT-2) are provided. Also provided are methods of producing the subject nucleic acid and protein compositions. The subject polypeptide and nucleic acid compositions find use in a variety of applications, including diagnostic and therapeutic agent screening applications, as well as in treatment therapies for disease conditions associated with ACAT-2 activity, e.g., in the treatment of gall stones.

6 Claims, No Drawings

OTHER PUBLICATIONS

Anderson, et al., (1998) "Identification of a Form of Acyl–CoA:Cholesterol Acyltransferase Specific to Liver and Intestine in Nonhuman Primates," *Journal of Biological Chemistry* vol. 273(41):26747–26754.

Cases, et al., (Oct. 9, 1998) "ACAT–2, A Second Mammalian Acyl–CoA:Cholesterol Acyltransferase," *Journal of Biological Chemistry* vol. 273(41):26755–26764.

Chang, et al., (Dec. 25, 1998) "Recombinant Acyl–CoA:cholesterol Acyltransferase–1 (ACAT–1) Purified to Essential Homogeneity Utilizes Cholesterol in Mixed Micelles or in Vesicles in a Highly Cooperative Manner," *Journal of Biological Chemistry* vol. 273(52):35132–35141.

Erickson, et al., (Oct. 1980) "Acyl–Coenzyme A: Cholesterol Acyltransferase in Human Liver. In Vitro Detection and Some Characteristics of the Enzyme," *Metabolism* vol. 29(10):991–996.

Farese, (1998) "Acyl CoA: Cholesterol Acyltransferase Genes and Knockout Mice," *Curr Opin Lipidol* vol. 9:119–123.

Meiner, et al., (1997) "Tissue Expression Studies on the Mouse acyl–CoA: Cholesterol Acyltransferase Gene (Acact): Findings Supporting the Existence of Multiple Cholesterol Esterfication Enzymes in Mice," *Journal of Lipid Research* vol. 38:1928–1933.

Meiner, et al., (Nov. 1996) "Disruption of the acyl–CoA: Cholesterol Acyltransferase Gene in Mice: Evidence Suggesting Multiple Cholesterol Esterification Enzymes in Mammals," *Proc. Natl. Acad. Sci. USA,* vol. 93(24):14041–14046.

Oelkers, et al., (1998) "Characterization of Two Human Genes Encoding Acyl Coenzyme A: Cholesterol Acyltransferase–related Enzymes," *Journal of Biological Chemistry* vol. 273(41):26765–26771.

Roark, et al., (1993) "Inhibitors of Acyl–CoA: Cholesterol Acyltransferase (ACAT). 2. Modification of Fatty Acid Anilide ACAT Inhibitors: Bioisoteric Replacement of the Amide Bond," *J. Med. Chem.* vol. 36:1662–1668.

Suckling, (1984–85) "Cholesterol Esterification and Hydrolysis in the Adrenal Cortex–The Role of ACYL–CoA: Cholesterol Acyltransferase," *Endocrine Research* vol. 10(3, 4):507–514.

Tabas, et al., (1988) "Acyl Coenzyme A: Cholesterol Acyl Transferase in Macrophages Utilizes a Cellular Pool of Cholesterol Oxidase–accessible Cholesterol as Substrate," *Journal of Biological Research* vol. 263(3):1266–1272.

Uelmen, et al., (1995) "Tissue–Specific Expression and Cholesterol Regulation of Acylcoenzyme A: Cholesterol Acyltransferase (ACAT) in Mice," *Journal of Biological Chemistry* vol. 270(44):26192–26201.

Gen Bank Accession No. AF099031 (May 20, 1999), "Homo Sapiens Acyl Co–A: Cholesterol Acyltransferase–2 (ACAT2) mRNA, complete cds."

Gen Bank Accession No. AA133152 (May 14, 1997), "zk97a05.s1 Soares_pregnant_uterus_NbHPU Homo sapiens cDNA clone IMAGE:490736 3' similar to TR:G461132 G461132 ACAT–2=Acetyl –CoA Acetyltransferase, TCP–1X {3' Region, Overlapping Region}; contains Alu repetitive element;, mRNA sequence."

Gen Bank Accession No. AA502423 (Aug. 18, 1997), "ng22d09.s1 NCI_CGAP_Ov2 Homo sapiens cDNA clone Image:930161 similar to TR:G461132 G461132 ACAT–2= Acetyl–CoA Actyltransferase, TCP–1X {3' Region, Overlapping Region)};, mRNA sequence."

Gen Bank Accession No. AF078751 (Oct. 15, 1998), "Mus musculus acyl coenzyme A: cholesterol acyltransferase–2 (Acact–2) mRNA, complete cds."

Gen Bank Accession No. S67969 (Mar. 16, 1994), "Acat–2= acetyl–CoA acetyltransferase, Tcp–1x {3' region, overlapping region} [mice, Genomic, 370nt]."

Gen Bank Accession No. AAC78335 (May 20, 1999), "acyl Co–A: cholesterol acyltransferase–2.".

Gen Bank Accession No. AAC64057 (Oct. 7, 1998), "acyl coenzyme A: cholesterol acyltransferase–2".

DeWitt S. Goodman, "Cholesterol Ester Metabolism" *Physiological Reviews,* Oct. 1965, Vol 45. No. 4, pp. 747–839.

Suckling and Strange, "Role of acyl–CoA; cholesterol acyltransferase in cellular cholesterol metabolism" *Journal of Lipid Research,* vol. 26, 1985, pp. 647–671.

T.Y. Chang et al. "ACYL–Coenzyme A; Cholesterol Acyltransferase" *Annu. Rev.Biochem,* 1997 66:613–38.

Field, et al. "Regulation of Cholesterol Metabolism in the Intestine" *Gastroenterology,* 1990; 99:539–551.

Wilson et al. "Review of cholesterol absorption with emphasis on dietary and biliary cholesterol" *Journal of Lipid Research,* vol. 35, 1994, pp. 943–955.

Dixon and Ginsberg, "Regulation of hepatic secretion of apolipoprotein B–containing lipoproteins; information obtained from cultured liver cells" *Journal of Lipid Research*, vol. 34, 1993, pp. 167–179.

Brown and Goldstein, "Lipoprotein Metabolism in the Macrophage: Implications for Cholesterol Deposition in Atherosclerosis" *Annu. Review Biochem.,* 1983, 52:223–61.

* cited by examiner

ACYL COA:CHOLESTEROL ACYLTRANSFERASE (ACAT-2)

CROSS REFERENCE TO RELATED APPLICATIONS

This application is a continuation-in-part application of U.S. patent application Ser. No. 09/328,857, filed Jun. 8, 1999; which application, pursuant to 35 U.S.C. § 119 (e), claims priority to the filing date of the U.S. Provisional Patent Application Serial No. 60/090,354 filed Jun. 23, 1998, the disclosure of which is herein incorporated by reference.

ACKNOWLEDGMENT OF GOVERNMENT SUPPORT

This invention was made with Government support under Grant Nos. R01 52069 and H157170 awarded by the National Institute of Health. The Government has certain rights in this invention.

INTRODUCTION

1. Field of the Invention

The field of the invention is enzymes, particularly acyltransferases.

BACKGROUND OF THE INVENTION

The ability to synthesize sterol esters is fundamental to most eukaryotic cells. Sterol esterification is thought to participate in the maintenance of cell membrane sterols at levels optimal for normal cell function. In mammalian cells, cholesterol esterification is catalyzed by the enzyme acyl CoA:cholesterol acyltransferase (E.C. 2.3.1.26, ACAT).

ACAT activity has been implicated in a number of physiologic processes. In the small intestine, ACAT has been proposed to play a role in cholesterol absorption by maintaining a free cholesterol diffusion gradient across the enterocyte surface through the intracellular formation of cholesterol esters. Cholesterol ester formation by ACAT has also been hypothesized to be important for the assembly and secretion of apolipoprotein B-containing lipoproteins in the intestine and the liver. In the adrenal glands and other steroidogenic tissues, ACAT synthesizes cholesterol esters that accumulate in cytosolic droplets where they can serve as cholesterol substrate stores for steroidogenesis. In macrophages, ACAT generates intracellular cholesterol esters that are stored as cytosolic lipid droplets, a characteristic feature of macrophage foam cells in atherosclerotic lesions.

Recent evidence has suggested that more than one ACAT exists in mammals. A human ACAT cDNA was first identified from a macrophage cDNA library. The disruption of the mouse homolog of this ACAT gene (Acact) yielded viable, ACAT-deficient (Acact$^{-/-}$) mice that were characterized by tissue-specific reductions in cholesterol esters. Cholesterol ester stores were markedly reduced in adrenal cortices and cultured peritoneal macrophages; however, substantial levels of ACAT activity were present in Acact($^{-/-}$ livers, and intestinal cholesterol absorption was normal, indicating that another ACAT enzyme was active in these tissues. Studies examining the tissue distribution of Acact mRNA expression also supported the hypothesis that more than one ACAT exists, as did previous biochemical and ACAT inhibitor studies showing differences between liver and aorta/macrophage ACAT activities. The above results indicate that a second ACAT enzyme contributes to cholesterol esterification activity in the liver and small intestine. As such, there is much interest in the identification, isolation and characterization of this putative second ACAT enzyme.

Relevant Literature

U.S. Pat. No. 5,484,727 reports the cloning of the Human ACAT-1 gene.

Farese, "Acyl CoA:cholesterol acyltransferase genes and knockout mice," Curr Opin Lipidol (1998 April) 9(2) :119–123, provides a review of the current knowledge of ACAT genes.

ACAT-1 is described in Goodman, D. S., Physiol. Rev. (1965) 45: 747–839; Suckling & Strange, J. Lipids Res. (1985) 26:647–671 and Chang et al., Annu. Rev. Biochem. (1997) 66: 613–638; Meiner et al., "Disruption of the acyl-CoA:cholesterol acyltransferase gene in mice: evidence suggesting multiple cholesterol esterification enzymes in mammals," Proc Natl Acad Sci USA (Nov. 26, 1996) 93(24):14041–14046; Meiner et al., "Tissue expression studies on the mouse acyl-CoA:cholesterol acyltransferase gene (Acact): findings supporting the existence of multiple cholesterol esterification enzymes in mice," J Lipid Res (1997 September) 38(9):1928–1933; Erickson et al., "Acylcoenzyme A:cholesterol acyltransferase in human liver. In vitro detection and some characteristics of the enzyme," Metabolism (1980, Octuber)29(10):991–996; Tabas et al., "Acyl coenzyme A:cholesterol acyl transferase in macrophages utilizes a cellular pool of cholesterol oxidase-accessible cholesterol as substrate," J Biol Chem (Jan. 25, 1988) 263(3):1266–1272; and Uelmen et al., "Tissue-specific expression and cholesterol regulation of acylcoenzyme A:cholesterol acyltransferase (ACAT) in mice. Molecular cloning of mouse ACAT cDNA, chromosomal localization, and regulation of ACAT in vivo and in vitro," J Biol Chem (Nov. 3, 1995) 270(44):26192–26201.

The role of ACAT in various biological processes is discussed in: Field et al., Gastroenterology (1990) 99:539–551; Wilson et al., J. Lipid Res. (1994) 35:943–955; Dixon & Ginsberg, Annu. Rev. Biochem. (1993) 34:167–179; Brown & Goldstein, Annu. Rev. Biochem. (1983) 52:223–261.

SUMMARY OF THE INVENTION

Nucleic acid compositions encoding novel ACAT proteins, as well as the novel ACAT-2 proteins, (ACAT-2) are provided. Also provided are methods of producing the subject nucleic acid and protein compositions. The subject polypeptide and nucleic acid compositions find use in a variety of applications, including diagnostic and therapeutic agent screening applications, as well as in treatment therapies for disease conditions associated with ACAT-2 activity, e.g., in the treatment of gall stones.

DETAILED DESCRIPTION OF THE INVENTION

Nucleic acid compositions encoding novel ACAT proteins, as well as the novel ACAT-2 proteins, (ACAT-2) are provided. Also provided are methods of producing the subject nucleic acid and protein compositions. The subject polypeptide and nucleic acid compositions find use in a variety of applications, including diagnostic and therapeutic agent screening applications, as well as in treatment therapies for disease conditions associated with ACAT-2 activity, e.g., in the treatment of gall stones.

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

NUCLEIC ACID COMPOSITIONS

Nucleic acid compositions encoding polypeptide products (hereinafter ACAT-2 and described in greater detail below), as well as fragments thereof, are provided. By nucleic acid composition is meant a composition comprising a sequence of DNA having an open reading frame that encodes an ACAT-2 polypeptide, i.e. a gene encoding a polypeptide having ACAT activity, where the encoded polypeptide is not ACAT-1 as disclosed in U.S. Pat. No: 5,484,727, the disclosure of which is herein incorporated by reference, and is capable, under appropriate conditions, of being expressed as an ACAT-2 polypeptide. Also encompassed in this term are nucleic acids that are homologous, substantially similar or identical to the nucleic acids encoding ACAT-2 polypeptides or proteins. Thus, the subject invention provides genes encoding mammalian ACAT-2, such as genes encoding human ACAT-2 and homologs thereof and mouse Acat-2 and homologs thereof.

The coding sequence of the mouse Acat-2 gene, i.e. the mouse cDNA encoding the mouse Acat-2 enzyme, has the nucleic acid sequence identified in U.S. patent application Ser. No. 09/328,857; the disclosure of which is herein incorporated by reference. Acat-2 maps to mouse chromosome 15. The coding sequence of the human ACAT-2 gene, i.e. the human cDNA encoding the human ACAT-2 enzyme, has the nucleic acid sequence identified in U.S. patent application Ser. No. 09/328,857; the disclosure of which is herein incorporated by reference. Of interest in many embodiments is a nucleic acid (or the complement thereof) that hybridizes with either of these sequences under stringent conditions, where stringent conditions are defined below.

The source of homologous genes to those specifically listed above may be any mammalian species, e.g., primate species, particularly human; rodents, such as rats and mice, canines, felines, bovines, ovines, equines, yeast, nematodes, etc. Between mammalian species, e.g., human and mouse, homologs have substantial sequence similarity, e.g. at least 75% sequence identity, usually at least 90%, more usually at least 95% between nucleotide sequences. Sequence similarity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithms for sequence analysis are known in the art, such as BLAST, described in Altschul et al. (1990), *J. Mol. Biol.* 215:403–10, etc. Unless specified otherwise, all sequence identity values provided herein are determined using GCG (Genetics Computer Group, Wisconsin Package, Standard Settings, gap creation penalty 3.0, gap extension penalty 0). The sequences provided herein are essential for recognizing ACAT-2 related and homologous polynucleotides in database searches.

Nucleic acids encoding the ACAT-2 proteins and ACAT-2 polypeptides of the subject invention may be cDNAs or genomic DNAs, as well as fragments thereof. The term "ACAT-2- gene" shall be intended to mean the open reading frame encoding specific ACAT-2 proteins and polypeptides, and ACAT-2 introns, as well as adjacent 5' and 3' non-coding nucleotide sequences involved in the regulation of expression, up to about 20 kb beyond the coding region, but possibly further in either direction. The gene may be introduced into an appropriate vector for extrachromosomal maintenance or for integration into a host genome.

The term "cDNA" as used herein is intended to include all nucleic acids that share the arrangement of sequence elements found in native mature mRNA species, where sequence elements are exons and 3' and 5' non-coding regions. Normally mRNA species have contiguous exons, with the intervening introns, when present, being removed by nuclear RNA splicing, to create a continuous open reading frame encoding an ACAT-2 protein.

A genomic sequence of interest comprises the nucleic acid present between the initiation codon and the stop codon, as defined in the listed sequences, including all of the introns that are normally present in a native chromosome. It may further include the 3' and 5' untranslated regions found in the mature mRNA. It may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of 100 kbp or smaller; and substantially free of flanking chromosomal sequence. The genomic DNA flanking the coding region, either 3' or 5', or internal regulatory sequences as sometimes found in introns, contains sequences required for proper tissue and stage specific expression.

The nucleic acid compositions of the subject invention may encode all or a part of the subject ACAT-2 proteins and polypeptides, described in greater detail infra. Double or single stranded fragments may be obtained from the DNA sequence by chemically synthesizing oligonucleotides in accordance with conventional methods, by restriction enzyme digestion, by PCR amplification, etc. For the most part, DNA fragments will be at least 15 nt, usually at least 18 nt or 25 nt, and may be at least about 50 nt. Of interest in certain embodiments are fragments which encode the N terminal portion of the encoded ACAT-2 protein, as described in greater detail infra, where the N-terminal portion may be at least about the N-terminal 25, 50, 75, 80, 85, 90 or 95 residues. Of interest in other embodiments are fragments which encode the C-terminal portion of the ACAT-2 protein, where the C-terminal portion may be at least about the C-terminal 100, 200, 300, 400 or 410 residues. Also of interest are nucleic acids in which the above N and C terminal encoding fragments flank an additional nucleic acid sequence, where this additional nucleic acid sequence may be anywhere from 10 to 200, usually from about 50 to 150 and more usually from about 50 to 100 nucleotides in length.

The ACAT-2 genes of the subject invention are isolated and obtained in substantial purity, generally as other than an intact chromosome. Usually, the DNA will be obtained substantially free of other nucleic acid sequences that do not include an ACAT-2 sequence or fragment thereof, generally being at least about 50%, usually at least about 90% pure and are typically "recombinant", i.e. flanked by one or more nucleotides with which it is not normally associated on a naturally occurring chromosome.

In addition to the plurality of uses described in greater detail in following sections, the subject nucleic acid compositions find use in the preparation of all or a portion of the ACAT-2 polypeptides, as described below.

POLYPEPTIDE COMPOSITIONS

Also provided by the subject invention are polypeptides having ACAT-2 activity, i.e. capable of catalyzing the esterification of cholesterol, as well as oxysterols, with fatty acyl CoA substrates. In addition to being capable of catalyzing the esterification of cholesterol with a fatty acyl CoA substrates, the subject proteins are incapable of esterifying, at least to any substantial extent, the following substrates: ethanol, retinol, tocopherol, β-sitoserol, lanosterol, vitamins D1 and D2, or diacylglycerol. With respect to fatty acyl CoA substrates, the ACAT-2 polypeptides exhibit the following preference: palmitoyl≧linoleoyl≧oleoyl≧arachindonyl. With ACAT-2 polypeptides, linoleoyl and palmitoyl compete with oleoyl for incorporation into cholesterol esters, but arachindonyl competes less well. In certain in vitro assays (see those reported in the Experimental Section, infra), the subject ACAT-2 polypeptides exhibit higher activity with oleoyl than with palmitoyl.

The term polyeptide composition as used herein refers to both the full length proteins as Well as portions or fragments thereof Also included in this term are variations of the naturally occurring proteins, where such variations are homologous or substantially similar to the naturally occurring protein, as described in greater detail below, be the naturally occurring protein the human protein, mouse protein, or protein from some other species which naturally expresses an ACAT-2 enzyme, usually a mammalian species. In the following description of the subject invention, the term ACAT-2 is used to refer not only to the human form of the enzyme, but also to homologs thereof expressed in non-human species, e.g. murine, rat and other mammalian species.

The subject ACAT-2 proteins are, in their natural environment, trans-membrane proteins. The subject proteins are characterized by the presence of at least one potential tyrosine phosphorylation site present in the motif MK-X-H/Y-SF, and multiple hydrophobic domains, including 5 to 10, usually 6 to 9 hydrophobic domains capable of serving as trans-membrane regions. The proteins range in length from about 400 to 650, usually from about 475 to 525 and more usually from about 485 to 500 amino acid residues, and the projected molecular weight of the subject proteins based solely on the number of amino acid residues in the protein ranges from about 50 to 80, usually from about 55 to 75 and more usually from about 60 to 65 kDa, where the actual molecular weight may vary depending on the amount of glycolsylation, if any, of the protein and the apparent molecular weight may be considerably less (40 to 50 kDa) due to SDS binding on gels.

The amino acid sequences of the subject proteins are characterized by having at least some homology to a corresponding ACAT-1 protein from the same species, e.g. a human ACAT-2 protein has at least some sequence homology with the human ACAT-1 protein, the mouse ACAT-2 protein has at least some sequence homology with the mouse Acat-1 protein, etc., where the sequence homology will not exceed about 80%, and usually will not exceed about 70% and more usually will not exceed about 60%, but will be at least about 30% and more usually at least about 40%, as determined using GCG (Genetics Computer Group, Wisconsin Package, Standard Settings, gap creation penalty 3.0, gap extension penalty 0.1).

Of particular interest in many embodiments are proteins that are non-naturally glycosylated. By non-naturally glycosylated is meant that the protein has a glycosylation pattern, if present, which is not the same as the glycosylation pattern found in the corresponding naturally occurring protein. For example, human ACAT-2 of the subject invention and of this particular embodiment is characterized by having a glycosylation pattern, if it is glycosylated at all, that differs from that of naturally occurring human ACAT-2. Thus, the non-naturally glycosylated ACAT-2 proteins of this embodiment include non-glycosylated ACAT-2 proteins, i.e. proteins having no covalently bound glycosyl groups.

The activity of the ACAT-2 protein is inhibited by a number of different compounds, including non-specific inhibitors, such as PMSF, PHMB and progesterone, and specific inhibitors, such as PD 132301–2, CI-976 and CI-1011. ACAT-2 is more sensitive to CI-976 and CI-1011 than ACAT-1, having an $IC_{50}$ value that is typically less than half that observed with ACAT-1 in the presence of the same inhibitor.

Of particular interest in certain embodiments,is the mouse ACAT-2 protein, where the mouse ACAT-2 protein of the subject invention has an amino acid sequence that is substantially the same as or identical to the sequence appearing in U.S. patent application Ser. No. 09/328,857; the disclosure of which is herein incorporated by reference. By substantially the same as is meant a protein having a sequence that has at least about 80%, usually at least about 90% and more usually at least about 98% sequence identity with this sequence, as measured by GCG, supra. Of particular interest are proteins encoded by a nucleic acid (or the complement thereof) that hybridize to the specific ACAT-2 nuclic acid sequences referenced above under stringent conditions (defined infra).

Of particular interest in other embodiments is the human ACAT-2 protein, where the human ACAT-2 protein of the subject invention has an amino acid sequence that is substantially the same as, or identical to, the sequence appearing in U.S. patent application Ser. No. 09/328,857; the disclosure of which is herein incorporated by reference. Of particular interest are proteins encoded by a nucleic acid (or the complement thereof) that hybridizes to the human nucleic acid ACAT-2 sequence identified above under stringent conditions (defined infra).

In addition to the specific ACAT-2 proteins described above, homologs or proteins (or fragments thereof) from other species, i.e. other animal or plant species, are also provided, where such homologs or proteins may be from a variety of different types of species, usually mammals, e.g. rodents, such as mice, rats; domestic animals, e.g. horse, cow, dog, cat; and humans. By homolog is meant a protein having at least about 35 %, usually at least about 40% and more usually at least about 60 % amino acid sequence identity the specific ACAT-2 proteins identified in U.S. patent application Ser. No. 09/328,857, where sequence identity is determined using the GCG, supra.

The ACAT-2 proteins of the subject invention (e.g. human ACAT-2, mouse ACAT-2 or homologs thereof) are present in a non-naturally occurring environment, e.g. are separated from their naturally occurring environment. In certain embodiments, the subject ACAT-2 protein is present in a composition that is enriched for ACAT-2 as compared to ACAT-2 in its naturally occurring environment. As such, purified ACAT-2 is provided, where by purified is meant that ACAT-2 is present in a composition that is substantially free of non ACAT-2 proteins, where by substantially free is meant that less than 90%, usually less than 60% and more usually less than 50% of the composition is made up of non-ACAT-2 proteins.

In certain embodiments of interest, the ACAT-2 protein is present in a composition that is substantially free of the constituents that are present in its naturally occurring environment. For example, a human ACAT-2 protein comprising composition according to the subject invention in this embodiment will be substantially, if not completely, free of those other biological constituents, such as proteins, carbohydrates, lipids, etc., with which it is present in its natural environment. As such, protein compositions of these embodiments will necessarily differ from those that are prepared by purifying the protein from a naturally occurring source, where at least trace amounts of the protein's constituents will still be present in the composition prepared from the naturally occurring source.

The ACAT-2 of the subject invention may also be present as an isolate, by which is meant that the ACAT-2 is substantially free of both non-ACAT-2 proteins and other naturally occurring biologic molecules, such as oligosaccharides, polynucleotides and fragments thereof, and the like, where substantially free in this instance means that less than 70%, usually less than 60% and more usually less than 50% of the composition containing the isolated ACAT-2 is a non-ACAT-2 naturally occurring biological molecule. In certain embodiments, the ACAT-2 is present in substantially pure form, where by substantially pure form is meant at least 95%, usually at least 97% and more usually at least 99% pure.

In addition to the naturally occurring ACAT-2 proteins, ACAT-2 polypeptides which vary from the naturally occurring ACAT-2 proteins are also provided. By ACAT-2 polypeptides is meant proteins having an amino acid sequence encoded by an open reading frame (ORF) of an ACAT-2 gene, described supra, including the full length ACAT-2 protein and fragments thereof, particularly biologically active fragments and/or fragments corresponding to functional domains; and including fusions of the subject polypeptides to other proteins or parts thereof Fragments of interest will typically be at least about 10 aa in length, usually at least about 50 aa in length, and may be as long as 300 aa in length or longer, but will usually not exceed about 1000 aa in length, where the fragment will have a stretch of amino acids that is identical to an ACAT-2 protein as provided in U.S. patent application Ser. No. 09/328,857, or a homolog thereof; of at least about 10 aa, and usually at least about 15 aa, and in many embodiments at least about 50 aa in length. In certain embodiments, N-terminal fragments of the ACAT-2 protein are of interest, e.g. fragments of the N-terminal 25, 50, 75, 80, 85, 90 or 95 residues. Of interest in other embodiments are fragments the C-terminal portion of the ACAT-2 protein, where the C-terminal portion may be at least about the C-terminal 100, 200, 300, 400 or 410 residues. Also of interest are fusion proteins of at least one of, or both of, the above C and N terminal fragments with an additional polypeptide sequence. In certain embodiments, of interest is a fusion protein in which the above N and C terminal fragments flank an additional sequence, where this additional sequence may be anywhere, from about 3 to 75, usually from about 10 to 50 and more usually from about 10 to 30 residues in length.

PREPARATION OF ACAT-2 POLYPEPTIDES

The subject ACAT-2 proteins and polypeptides may be obtained from naturally occurring sources, but are preferably synthetically produced. Where obtained from naturally occurring sources, the source chosen will generally depend on the species from which the ACAT-2 is to be derived.

The subject ACAT-2 polypeptide compositions may be synthetically derived by expressing a recombinant gene encoding ACAT-2, such as the polynucleotide compositions described above, in a suitable host. For expression, an expression cassette may be employed. The expression vector will provide a transcriptional and translational initiation region, which may be inducible or constitutive, where the coding region is operably linked under the transcriptional control of the transcriptional initiation region, and a transcriptional and translational termination region. These control regions may be native to an ACAT-2 gene, or may be derived from exogenous sources.

Expression vectors generally have convenient restriction sites located near the promoter sequence to provide for the insertion of nucleic acid sequences encoding heterologous proteins. A selectable marker operative in the expression host may be present. Expression vectors may be used for the production of fusion proteins, where the exogenous fusion peptide provides additional functionality, i.e. increased protein synthesis, stability, reactivity with defined antisera, an enzyme marker, e.g. galactosidase, etc.

Expression cassettes may be prepared comprising a transcription initiation region, the gene or fragment thereof, and a transcriptional termination region. Of particular interest is the use of sequences that allow for the expression of functional epitopes or domains, usually at least about 8 amino acids in length, more usually at least about 15 amino acids in length, to about 25 amino acids, and up to the complete open reading frame of the gene. After introduction of the DNA, the cells containing the construct may be selected by means of a selectable marker, the cells expanded and then used for expression.

ACAT-2 proteins and polypeptides may be expressed in prokaryotes or eukaryotes in accordance with conventional ways, depending upon the purpose for expression. For large scale production of the protein, a unicellular organism, such as *E. coli, B. subtilis, S. cerevisiae*, insect cells in combination with baculovirus vectors, or cells of a higher organism such as vertebrates, particularly mammals, e.g. COS 7 cells, may be used as the expression host cells. In some situations, it is desirable to express the ACAT-2 gene in eukaryotic cells, where the ACAT-2 protein will benefit from native folding and post-translational modifications. Small peptides can also be synthesized in the laboratory. Polypeptides that are subsets of the complete ACAT-2 sequence may be used to identify and investigate parts of the protein important for function.

Once the source of the protein is identified and/or prepared, e.g. a transfected host expressing the protein is prepared, the protein is then purified to produce the desired ACAT-2 comprising composition. Any convenient protein purification procedures may be employed, where suitable protein purification methodologies are described in Guide to Protein Purification, (Deuthser ed.) (Academic Press, 1990). For example, a lysate may be prepared from the original source, e.g. naturally occurring cells or tissues that express ACAT-2 or the expression host expressing ACAT-2, and purified using HPLC, exclusion chromatography, gel electrophoresis, affinity chromatography, and the like.

USES OF THE SUBJECT ACAT-2 POLYPEPTIDE AND NUCLEIC ACID COMPOSITIONS

The subject polypeptide and nucleic acid compositions find use in a variety of different applications, including diagnostic and therapeutic agent screening/discovery/preparation applications, as well as the treatment of disease conditions associated with ACAT-2 activity.

GENERAL APPLICATIONS

The subject nucleic acid compositions find use in a variety of general applications. General applications of interest include: (a) the identification of ACAT-2 homologs; (b) as a source of novel promoter elements; (c) the identification of ACAT-2 expression regulatory factors; (d) as probes and primers in hybridization applications, e.g. PCR; (e) the identification of expression patterns in biological specimens; (f) the preparation of cell or animal models for ACAT-2 function; (g) the preparation of in vitro models for ACAT-2 function; etc.

Identification of ACAT-2 Homologs

Homologs of ACAT-2 are identified by any of a number of methods. A fragment of the provided cDNA may be used as a hybridization probe against a cDNA library from the target organism of interest, where low stringency conditions are used. The probe may be a large fragment, or one or more short degenerate primers. Nucleic acids having sequence similarity are detected by hybridization under low stringency conditions, for example, at 50° C. and 6×SSC (0.9 M sodium chloride/0.09 M sodium citrate) and remain bound when subjected to washing at 55° C. in 1×SSC (0.15 M sodium chloride/0.015 M sodium citrate). Sequence identity may be determined by hybridization under stringent conditions, for example, at 50° C. or higher and 0.1×SSC (15 mM sodium chloride/01.5 mM sodium citrate). Nucleic acids having a region of substantial identity to the provided ACAT-2 sequences, e.g. allelic variants, genetically altered versions of the gene, etc., bind to the provided ACAT-2 sequences under stringent hybridization conditions. By using probes, particularly labeled probes of DNA sequences, one can isolate homologous or related genes.

Identification of Novel Promoter Elements

The sequence of the 5' flanking region may be utilized for promoter elements, including enhancer binding sites, that provide for regulation in tissues where ACAT-2 is expressed. The tissue specific expression is useful for determining the pattern of expression, and for providing promoters that mimic the native pattern of expression. Naturally occurring polymorphisms in the promoter region are useful for determining natural variations in expression, particularly those that may be associated with disease.

Identification of ACAT-2 Expression Regulatory Factors

Alternatively, mutations may be introduced into the promoter region to determine the effect of altering expression in experimentally defined systems. Methods for the identification of specific DNA motifs involved in the binding of transcriptional factors are known in the art, e.g. sequence similarity to known binding motifs, gel retardation studies, etc. For examples, see Blackwell et al. (1995), *Mol. Med.* 1:194–205; Mortlock et al. (1996), *Genome Res.* 6:327–33; and Joulin and Richard-Foy (1995), *Eur. J. Biochem.* 232:620–626.

The regulatory sequences may be used to identify cis acting sequences required for transcriptional or translational regulation of ACAT-2 expression, especially in different tissues or stages of development, and to identify cis acting sequences and trans-acting factors that regulate or mediate ACAT-2 expression. Such transcription or translational control regions may be operably linked to an ACAT-2 gene in order to promote expression of wild type or altered ACAT-2 or other proteins of interest in cultured cells, or in embryonic, fetal or adult tissues, and for gene therapy.

Probes and Primers

Small DNA fragments are useful as primers for PCR, hybridization screening probes, etc. Larger DNA fragments, i.e. greater than 100 nt are useful for production of the encoded polypeptide, as described in the previous section. For use in amplification reactions, such as PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

Identification of Expression Patterns in Biological Specimens

The DNA may also be used to identify expression of the gene in a biological specimen. The manner in which one probes cells for the presence of particular nucleotide sequences, as genomic DNA or RNA, is well established in the literature. Briefly, DNA or mRNA is isolated from a cell sample. The mRNA may be amplified by RT-PCR, using reverse transcriptase to form a complementary DNA strand, followed by polymerase chain reaction amplification using primers specific for the subject DNA sequences. Alternatively, the mRNA sample is separated by gel electrophoresis, transferred to a suitable support, e.g. nitrocellulose, nylon, etc., and then probed with a fragment of the subject DNA as a probe. Other techniques, such as oligonucleotide ligation assays, in situ hybridizations, and hybridization to DNA probes arrayed on a solid chip may also find use. Detection of mRNA hybridizing to the subject sequence is indicative of ACAT-2 gene expression in the sample.

The Preparation of ACAT-2 Mutants

The sequence of an ACAT-2 gene, including flanking promoter regions and coding regions, may be mutated in various ways known in the art to generate targeted changes in promoter strength, sequence of the encoded protein, etc. The DNA sequence or protein product of such a mutation will usually be substantially similar to the sequences provided herein, i.e. will differ by at least one nucleotide or amino acid, respectively, and may differ by at least two but not more than about ten nucleotides or amino acids. The sequence changes may be substitutions, insertions, deletions, or a combination thereof. Deletions may further include larger changes, such as deletions of a domain or exon. Other modifications of interest include epitope tagging, e.g. with the FLAG system, HA, etc. For studies of subcellular localization, fusion proteins with green fluorescent proteins (GFP) may be used.

Techniques for in vitro mutagenesis of cloned genes are known. Examples of protocols for site specific mutagenesis may be found in Gustin et al. (1993), *Biotechniques* 14:22; Barany (1985), *Gene* 37:111–23; Colicelli et al. (1985), *Mol. Gen. Genet.* 199:537–9; and Prentki et al. (1984), *Gene* 29:303–13. Methods for site specific mutagenesis can be found in Sambrook et al, *Molecular Cloning. A Laboratory Manual*, CSH Press 1989, pp. 15.3–15.108; Weiner et al. (1993), *Gene* 126:35–41; Sayers et al. (1992), *Biotechniques* 13:592–6; Jones and Winistorfer (1992), *Biotechniques* 12:528–30; Barton et al. (1990), *Nucleic Acicds Res* 18:7349–55; Marotti and Tomich (1989), *Gene Anal. Tech.* 6:67–70; and Zhu (1989), Anal Biochem 177:120–4. Such mutated genes may be used to study structure-function relationships of ACAT-2, or to alter properties of the protein that affect its function or regulation.

Production of in Vivo Models of ACAT-2 Function

The subject nucleic acids can be used to generate transgenic, non-human animals or site specific gene modifications in cell lines. Transgenic animals may be made through homologous recombination, where the normal Acat-2 locus is altered. Alternatively, a nucleic acid construct is randomly integrated into the genome. Vectors for stable integration include plasmids, retroviruses and other animal viruses, YACs, and the like.

The modified cells or animals are useful in the study of ACAT-2 function and regulation. For example, a series of small deletions and/or substitutions may be made in the host's native ACAT-2 gene to determine the role of different exons in cholesterol metabolism, e.g. cholesterol ester synthesis, cholesterol absorption, etc. Specific constructs of interest include anti-sense ACAT-2, which will block ACAT-2 expression, expression of dominant negative ACAT-2 mutations, and over-expression of ACAT-2 genes. Where an ACAT-2 sequence is introduced, the introduced sequence may be either a complete or partial sequence of an ACAT-2 gene native to the host, or may be a complete or partial ACAT-2 sequence that is exogenous to the host animal, e.g., a human ACAT-2 sequence. A detectable marker, such as lac Z, may be introduced into the acat-2 locus, where upregulation of ACAT-2 expression will result in an easily detected change in phenotype.

One may also provide for expression of the ACAT-2 gene or variants thereof in cells or tissues where it is not normally expressed, at levels not normally present in such cells or tissues, or at abnormal times of development.

DNA constructs for homologous recombination will comprise at least a portion of the ACAT-2 gene native to the species of the host animal, wherein the gene has the desired genetic modification(s), and includes regions of homology to the target locus. DNA constructs for random integration need not include regions of homology to mediate recombination. Conveniently, markers for positive and negative selection are included.

Methods for generating cells having targeted gene modifications through homologous recombination are known in the art. For various techniques for transfecting mammalian cells, see Keown et al. (1990), *Meth. Enzymol.* 185:527–537.

For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of leukemia inhibiting factor (LIF). When ES or embryonic cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting offspring screened for the construct. By providing for a different phenotype of the blastocyst and the genetically modified cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in in vitro culture. The transgenic animals may be any non-human mammal, such as laboratory animals, domestic animals, etc. The transgenic animals may be used in functional studies, drug screening, etc., e.g. to determine the effect of a candidate drug on ACAT-2 activity.

Production of In Vitro Models of ACAT-2 Function

One can also use the polypeptide compositions of the subject invention to produce in vitro models of ACAT-2 function, e.g. the ability to catalyze the esterification of cholesterol with a fatty acyl CoA substrate. Such models will generally at least include the subject ACAT-2 proteins and ACAT-2 substrates, such as cholesterol and fatty acyl

DIAGNOSTIC APPLICATIONS

Also provided are methods of diagnosing disease states associated with ACAT-2 activity, e.g. based on observed levels of ACAT-2 or the expression level of the ACAT-2 gene in a biological sample of interest. Samples, as used herein, include biological fluids such as semen, blood, cerebrospinal fluid, tears, saliva, lymph, dialysis fluid and the like; organ or tissue culture derived fluids; and fluids extracted from physiological tissues. Also included in the term are derivatives and fractions of such fluids. The cells may be dissociated, in the case of solid tissues, or tissue sections may be analyzed. Alternatively a lysate of the cells may be prepared.

A number of methods are available for determining the expression level of a gene or protein in a particular sample. Diagnosis may be performed by a number of methods to determine the absence or presence or altered amounts of normal or abnormal ACAT-2 in a patient sample. For example, detection may utilize staining of cells or histological sections with labeled antibodies, performed in accordance with conventional methods. Cells are permeabilized to stain cytoplasmic molecules. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Alternatively, the secondary antibody conjugated to a flourescent compound, e.g. fluorescein, rhodamine, Texas red, etc. Final detection uses a substrate that undergoes a color change in the presence of the peroxidase. The absence or presence of antibody binding may be determined by various methods, including flow cytometry of dissociated cells, microscopy, radiography, scintillation counting, etc.

Alternatively, one may focus on the expression of ACAT-2. Biochemical studies may be performed to determine whether a sequence polymorphism in an ACAT-2 coding region or control regions is associated with disease. Disease associated polymorphisms may include deletion or truncation of the gene, mutations that alter expression level, that affect the activity of the protein, etc.

Changes in the promoter or enhancer sequence that may affect expression levels of ACAT-2 can be compared to expression levels of the normal allele by various methods known in the art. Methods for determining promoter or enhancer strength include quantitation of the expressed natural protein; insertion of the variant control element into a vector with a reporter gene such as β-galactosidase, luciferase, chloramphenicol acetyltransferase, etc. that provides for convenient quantitation; and the like.

A number of methods are available for analyzing nucleic acids for the presence of a specific sequence, e.g. a disease associated polymorphism. Where large amounts of DNA are available, genomic DNA is used directly. Alternatively, the region of interest is cloned into a suitable vector and grown in sufficient quantity for analysis. Cells that express ACAT-2 may be used as a source of mRNA, which may be assayed directly or reverse transcribed into cDNA for analysis. The nucleic acid may be amplified by conventional techniques, such as the polymerase chain reaction (PCR), to provide sufficient amounts for analysis. The use of the polymerase chain reaction is described in Saiki, et al. (1985), *Science* 239:487, and a review of techniques may be found in Sambrook, et al. *Molecular Cloning: A Laboratory Manual*, CSH Press 1989, pp.14.2–14.33. Alternatively, various methods are known in the art that utilize oligonucleotide ligation as a means of detecting polymorphisms, for examples see Riley et al. (1990), *Nucl. Acids Res.* 18:2887–2890; and Delahunty et al (1996), *Am. J. Hum. Genet.* 58:1239–1246.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4', 5'-dichloro-6-carboxyfluorescein (JOE), 6-carboxy-X-rhodamine (ROX), 6-carboxy-2,',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}$P, $^{35}$S, $^{3}$H; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g. amplified or cloned fragment, is analyzed by one of a number of methods known in the art. The nucleic acid may be sequenced by dideoxy or other methods, and the sequence of bases compared to a wild-type ACAT-2 sequence. Hybridization with the variant sequence may also be used to determine its presence, by Southern blots, dot blots, etc. The hybridization pattern of a control and variant sequence -5-to an array of oligonucleotide probes immobilized on a solid support, as described in U.S. Pat. No. 5,445,934, or in WO 95/35505, may also be used as a means of detecting the presence of variant sequences. Single strand conformational polymorphism (SSCP) analysis, denaturing gradient gel electrophoresis (DGGE), and heteroduplex analysis in gel matrices are used to detect conformational changes created by DNA sequence variation as alterations in electrophoretic mobility. Alternatively, where a polymorphism creates or destroys a recognition site for a restriction endonuclease, the sample is digested with that endonuclease, and the products size fractionated to determine whether the fragment was digested. Fractionation is performed by gel or capillary electrophoresis, particularly acrylamide or agarose gels.

Screening for mutations in ACAT-2 may be based on the functional or antigenic characteristics of the protein. Protein truncation assays are useful in detecting deletions that may affect the biological activity of the protein. Various immunoassays designed to detect polymorphisms in ACAT-2 proteins may be used in screening. Where many diverse genetic mutations lead to a particular disease phenotype, functional protein assays have proven to be effective screening tools. The activity of the encoded ACAT-2 protein may be determined by comparison with the wild-type protein.

Diagnostic methods of the subject invention in which the level of ACAT-2 expression is of interest will typically involve comparison of the ACAT-2 nucleic acid abundance of a sample of interest with that of a control value to determine any relative differences, where the difference may be measured qualitatively and/or quantitatively, which differences are then related to the presence or absence of an abnormal ACAT-2 expression pattern. A variety of different methods for determining the nucleic acid abundance in a sample are known to those of skill in the art, where particular methods of interest include those described in: Pietu et al., Genome Res. (June 1996) 6: 492–503; Zhao et al., Gene (Apr. 24, 1995) 156: 207–213; Soares, Curr. Opin. Biotechnol. (October 1997) 8: 542–546; Raval, J. Pharmacol Toxicol Methods (November 1994) 32: 125–127; Chalifour et al., Anal. Biochem (Feb. 1, 1994) 216: 299–304; Stolz & Tuan, Mol. Biotechnol. (December 19960 6: 225–230; Hong et al., Bioscience Reports (1982) 2: 907; and McGraw, Anal. Biochem. (1984) 143: 298. Also of interest are the methods disclosed in WO 97/27317, the disclosure of which is herein incorporated by reference.

SCREENING ASSAYS

The subject ACAT-2 polypeptides find use in various screening assays designed to identify therapeutic agents. The screening methods will typically be assays which provide for qualitative/quantitative measurements of enzyme activity in the presence of a particular candidate therapeutic agent. For example, the assay could be an assay which measures the esterification activity of ACAT-2 in the presence and absence of a candidate inhibitor agent. The screening method may be an in vitro or in vivo format, where both formats are readily developed by those of skill in the art. Depending on the particular method, one or more of, usually one of, the components of the screening assay may be labeled, where by labeled is meant that the components comprise a detectable moiety, e.g. a fluorescent or radioactive tag, or a member of a signal producing system, e.g. biotin for binding to an enzyme-streptavidin conjugate in which the enzyme is capable of converting a substrate to a chromogenic product.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used.

A variety of different candidate agents may be screened by the above methods. Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

ACAT-2 NUCLEIC ACID AND POLYPEPTIDE THERAPEUTIC COMPOSITIONS

The nucleic acid compositions of the subject invention also find use as therapeutic agents in situations where one wishes to enhance ACAT-2 activity in a host, e.g. in a mammalian host in which ACAT-2 activty is sufficiently low such that a disease condition is present, etc. The ACAT-2 genes, gene fragments, or the encoded ACAT-2 protein or protein fragments are useful in gene therapy to treat disorders associated with ACAT-2 defects. Expression vectors may be used to introduce the ACAT-2 gene into a cell. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day, more usually for a period of at least about several days to several weeks.

The gene or ACAT-2 protein may be introduced into tissues or host cells by any number of routes, including viral infection, microinjection, or fusion of vesicles. Jet injection may also be used for intramuscular administration, as described by Furth et al (1992), *Anal Biochem* 205:365–368. The DNA may be coated onto gold microparticles, and delivered intradermally by a particle bombardment device, or "gene gun" as described in the literature (see, for example, Tang et al. (1992), *Nature* 356:152–154), where gold microprojectiles are coated with the DNA, then bombarded into skin cells.

METHODS OF MODULATING ACAT-2 ACTIVITY IN A HOST

Also provided are methods of regulating, including enhancing and inhibiting, ACAT-2 activity in a host. Where the ACAT-2 activity occurs in vivo in a host, an effective amount of active agent that modulates the activity, e.g. reduces the activity, of ACAT-2 in vivo, is administered to the host. In many embodiments, the active agent is ACAT-2 specific, e.g., an ACAT-2 specific inhibitor which inhibits ACAT2 activity but not other activities, such as ACAT-1 activity. The active agent may be a variety of different compounds, including a naturally occurring or synthetic small molecule compound, an antibody, fragment or derivative thereof, an antisense composition, and the like.

Naturally occurring or synthetic small molecule compounds of interest include numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Also of interest as active agents are antibodies that modulate, e.g. reduce, if not inhibit, ACAT-2 activity in the host. Suitable antibodies are obtained by immunizing a host animal with peptides comprising all or a portion of an ACAT-2 protein, such as found in the ACAT-2 polypeptide compositions of the subject invention. Suitable host animals include mouse, rat sheep, goat, hamster, rabbit, etc. The origin of the protein immunogen may be mouse, human, rat, monkey etc. The host animal will generally be a different species than the immunogen, e.g. human ACAT-2 used to immunize mice, etc.

The immunogen may comprise the complete protein, or fragments and derivatives thereof. Preferred immunogens comprise all or a part of ACAT-2, where these residues contain the post-translation modifications, such as glycosylation, found on the native ACAT-2. Immunogens comprising the extracellular domain are produced in a variety of ways known in the art, e.g. expression of cloned genes using conventional recombinant methods, isolation from HEC, etc.

For preparation of polyclonal antibodies, the first step is immunization of the host animal with ACAT-2, where the ACAT-2 will preferably be in substantially pure form, comprising less than about 1% contaminant. The immunogen may comprise complete ACAT-2, fragments or derivatives thereof. To increase the immune response of the host animal, the ACAT-2 may be combined with an adjuvant, where suitable adjuvants include alum, dextran, sulfate, large polymeric anions, oil& water emulsions, e.g. Freund's adjuvant, Freund's complete adjuvant, and the like. The ACAT-2 may also be conjugated to synthetic carrier proteins or synthetic antigens. A variety of hosts may be immunized to produce the polyclonal antibodies. Such hosts include rabbits, guinea pigs, rodents, e.g. mice, rats, sheep, goats, and the like. The ACAT-2 is administered to the host, usually intradermally, with an initial dosage followed by one or more, usually at least two, additional booster dosages. Following immunization, the blood from the host will be collected, followed by separation of the serum from the blood cells. The Ig present in the resultant antiserum may be further fractionated using known methods, such as ammonium salt fractionation, DEAE chromatography, and the like.

Monoclonal antibodies are produced by conventional techniques. Generally, the spleen and/or lymph nodes of an immunized host animal provide a source of plasma cells. The plasma cells are immortalized by fusion with myeloma cells to produce hybridoma cells. Culture supernatant from individual hybridomas is screened using standardtechniques to identify those producing antibodies with the desired specificity. Suitable animals for production of monoclonal antibodies to the human protein include mouse, rat, hamster, etc. To raise antibodies against the mouse protein, the animal will generally be a hamster, guinea pig, rabbit, etc. The antibody may be purified from the hybridoma cell supernatants or ascites fluid by conventional techniques, e.g. affinity chromatography using ACAT-2 bound to an insoluble support, protein A sepharose, etc.

The antibody may be produced as a single chain, instead of the normal multimeric structure. Single chain antibodies are described in Jost et al. (1994) *J.B.C.* 269:26267–73, and others. DNA sequences encoding the variable region of the heavy chain and the variable region of the light chain are ligated to a spacer encoding at least about 4 amino acids of small neutral amino acids, including glycine and/or serine. The protein encoded by this fusion allows assembly of a functional variable region that retains the specificity and affinity of the original antibody.

For in vivo use, particularly for injection into humans, it is desirable to decrease the antigenicity of the antibody. An immune response of a recipient against the blocking agent will potentially decrease the period of time that the therapy is effective. Methods of humanizing antibodies are known in the art. The humanized antibody may be the product of an animal having transgenic human immunoglobulin constant region genes (see for example International Patent Applications WO 90/10077 and WO 90/04036). Alternatively, the antibody of interest may be engineered by recombinant DNA techniques to substitute the CH1, CH2, CH3, hinge domains, and/or the framework domain with the corresponding human sequence (see WO 92/02190).

The use of Ig cDNA for construction of chimeric immunoglobulin genes is known in the art (Liu et al. (1987) *P.N.A.S.* 84:3439 and (1987) *J. Immunol.* 139:3521). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al. (199 1) *Sequences of Proteins of Immunological Interest*, N.I.H. publication no. 91–3242. Human C region genes are readily available from known clones. The choice of isotype will be guided by the desired effector functions, such as complement fixation, or activity in antibody-dependent cellular cytotoxicity. Preferred isotypes are IgG1, IgG3 and IgG4. Either of the human light chain constant regions, kappa or lambda, may be used. The chimeric, humanized antibody is then expressed by conventional methods.

Antibody fragments, such as Fv, F(ab')$_2$ and Fab may be prepared by cleavage of the intact protein, e.g. by protease or chemical cleavage. Alternatively, a truncated gene is designed. For example, a chimeric gene encoding a portion of the F(ab')$_2$ fragment would include DNA sequences encoding the CH1 domain and hinge region of the H chain, followed by a translational stop codon to yield the truncated molecule.

Consensus sequences of H and L J regions may be used to design oligonucleotides for use as primers to introduce useful restriction sites into the J region for subsequent linkage of V region segments to human C region segments. C region cDNA can be modified by site directed mutagenesis to place a restriction site at the analogous position in the human sequence.

Expression vectors include plasmids, retroviruses, YACs, EBV derived episomes, and the like. A convenient vector is one that encodes a functionally complete human CH or CL immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody may be joined to any strong promoter, including retroviral LTks, e.g. SV-40 early promoter, (Okayama et al. (1983) *Mol. Cell. Bio.* 3:280), Rous sarcoma virus LTR (Gorman et al (1982) *P.N.A.S.* 79:6777), and moloney murine leukemia virus LTR (Grosschedl et al. (1985) *Cell* 41:885); native Ig promoters, etc.

In yet other embodiments of the invention, the active agent is an agent that modulates, and generally decreases or down regulates, the expression of ACAT-2 in the host. Antisense molecules can be used to down-regulate expression of ACAT-2 in cells. The anti-sense reagent may be antisense oligonucleotides (ODN), particularly synthetic ODN having chemical modifications from native nucleic acids, or nucleic acid constructs that express such anti-sense molecules as RNA. The antisense sequence is complementary to the mRNA of the targeted gene, and inhibits expression of the targeted gene products. Antisense molecules inhibit gene expression through various mechanisms, e.g. by reducing the amount of mRNA available for translation, through activation of RNAse H, or steric hindrance. One or a combination of antisense molecules may be administered, where a combination may comprise multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996), *Nature Biotechnol.* 14:840–844).

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Antisense oligonucleotides may be chemically synthesized by methods known in the art (see Wagner et al. (1993), supra, and Milligan et al., supra.) Preferred oligonucleotides are chemically modified from the native phosphodiester structure, in order to increase their intracellular stability and binding affinity. A number of such modifications have been described in the literature, which alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2-5'-O-phosphonate and 3'-NH-5'-O-phosphoroamidate. Peptide nucleic acids replace the entire ribose phosphodiester backbone with a peptide linkage. Sugar modifications are also used to enhance stability and affinity. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine, 5-propynyl-2'-deoxyuridine and 5-propynyl-2'-deoxycytidine have been shown to increase affinity and biological activity when substituted for deoxythymidine and deoxycytidine, respectively.

As an alternative to anti-sense inhibitors, catalytic nucleic acid compounds, e.g. ribozymes, anti-sense conjugates, etc. may be used to inhibit gene expression. Ribozymes may be synthesized in vitro and administered to the patient, or may be encoded on an expression vector, from which the ribozyme is synthesized in the targeted cell (for example, see International patent application WO 9523225, and Beigelman et al. (1995), *Nucl. Acids Res.* 23:4434–42). Examples of oligonucleotides with catalytic activity are described in WO 9506764. Conjugates of anti-sense ODN with a metal complex, e.g. terpyridylCu(II), capable of mediating mRNA hydrolysis are described in Bashkin et al. (1995), *Appl. Biochem. Biotechnol.* 54:43–56.

As mentioned above, of particular interest in many embodiments are agents that selectively modulate ACAT-2 activity, i.e. agents that modulate the activity of ACAT-2 more than the activity of ACAT-1. In many embodiments, of interest are agents that modulate ACAT-2 activity with substantially no effect, including no effect, on ACAT-1 activity. Of particularly interest in many embodiments are agents that modulate by at least reducing, if not substantially inhibiting, ACAT-2 activity.

As mentioned above, an effective amount of the active agent is administered to the host, where "effective amount" means a dosage sufficient to produce a desired result, where the desired result in the desired modulation, e.g. enhancement, reduction, of ACAT-2 activity.

In the subject methods, the active agent(s) may be administered to the host using any convenient means capable of resulting in the desired inhibition of ACAT-2 activity. Thus, the agent can be incorporated into a variety of formulations for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

As such, administration of the agents can be achieved in various ways, including oral, buccal, rectal, parenteral, intraperitoneal, intradermal, transdermal, intracheal,etc., administration.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Where the agent is a polypeptide, polynucleotide, analog or mimetic thereof, e.g. antisense composition, it may be introduced into tissues or host cells by any number of routes, including viral infection, microinjection, or fusion of vesicles. Jet injection may also be used for intramuscular administration, as described by Furth et al. (1992), *Anal Biochem* 205:365–368. The DNA may be coated onto gold microparticles, and delivered intradermally by a particle bombardment device, or "gene gun" as described in the literature (see, for example, Tang et al (1992), *Nature* 356:152–154), where gold microprojectiles are coated with the ACAT-2 DNA, then bombarded into skin cells.

Those of skill in the art will readily appreciate that dose levels can vary as a function of the specific compound, the severity of the symptoms and the susceptibility of the subject to side effects. Preferred dosages for a given compound are readily determinable by those of skill in the art by a variety of means.

The subject methods find use in the treatment of a variety of different disease conditions involving ACAT-2 activity, including both insufficient or hypo-ACAT-2 activity and hyper-ACAT-2 activity. Of particular interest is the use of the subject invention to treat patients suffering from disease conditions associated with hyper-ACAT-2 activity, such as disease conditions associated with the presence of elevated cholesterol ester levels, e.g. hypercholesterolemia or hyperlipidemia, including hypertriglyceridemia. In other words, of interest is the use of the subject invention to treat patients suffereing from a disease condition where it is desirable to reduce ACAT-2 activity. In many embodiments, the disease conditions will be those in which it is desired to selectively inhibit ACAT-2 activity and not ACAT-1 activity. Other disease conditions include atherosclerosis. The subject compositions may also be used to modulate the immune response in a host, e.g. the immune response of macrophages, where conditions in which such modulation is desirable include immune related diseases, e.g. rheumatoid arthritis, multiple sclerosis, as well as infectious diseases, e.g. toxoplasmosis.

Of particular interest in many embodiments is the use of the subject methods to at least reduce, if not substantially or completely eliminate ACAT activity in the liver and/or small intestine. In these embodiments, the subject methods are employed to at least reduce, if not substantially or completely eliminate, diet induced hypercholesterolemia and/or gall stone formation in the host being treated. In addition, the subject methods may be employed to reduce or lower plasma cholesterol levels. In these methods, of particular interest is the use of ACAT-2 selective inhibitors.

By treatment is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as hypercholesterolemia, etc. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

A variety of hosts are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

Kits with unit doses of the active agent, usually in oral or injectable doses, are provided. In such kits, in addition to the containers containing the unit doses will be an informational package insert describing the use and attendant benefits of the drugs in treating pathological condition of interest. Preferred compounds and unit doses are those described herein above.

The following examples are offered primarily for purposes of illustration. It will be readily apparent to those skilled in the art that the formulations, dosages, methods of administration, and other parameters of this invention may be further modified or substituted in various ways without departing from the spirit and scope of the invention.

EXPERIMENTAL

1. Mouse and Human ACAT2 was Cloned and Characterized as Described in U.S. patent application Ser. No. 09/328,857; the Disclosure of Which is Herein Incorporated by Reference II. Further Characterization As demonstrated above, ACAT2 expression is restricted to the small intestine and liver. See also Anderson, et al, *J. Biol. Chem.* 273, 26747–26754 (1998); Cases, et al., *J. Biol. Chem.* 273, 26755–26764 (1998); and P. Oelkers et al., J. Biol. Chem. 273, 26765–26771 (1998). Given this expression pattern and the ACAT1$^{-/-}$ phenotype, we hypothesized that ACAT2 is the major ACAT in mouse small intestine and liver, where it plays a regulatory role in intestinal cholesterol absorption and in the synthesis and secretion of apolipoprotein B (apoB)-containing lipoproteins. To test this hypothesis, we generated ACAT2-deficient (ACAT2$^{-/-}$) mice using a vector that replaced the C-terminal coding sequences of ACAT2 with neo.

Briefly, a P1 bacteriophage clone containing mouse ACAT2 was obtained (Research Genetics), and a ~16-kb Spel fragment was subcloned into pBSSKII. A sequence replacement vector was constructed in pNTKIoxP [(a modified version of pNTK (see R. Mortensen, in *Current Protocols in Molecular Biology* F. M. Ausubel, et al., Ed.,§Eds., (John Wiley & Sons, New York, 1999), vol. 2, pp. 9.16.1–9.16.11) that was provided by Yao-Wu Zheng, University of California, San Francisco] by amplifying and subcloning a 1.6-kb upstream short-arm fragment containing 3' coding sequences (primers: sense, 5'-cgcggatccGGCTCTGCTGCTCTCCATCTTGCA-3' (SEQ ID NO:0 1) and antisense 5'-cgcggatccgaacaTCCTGTCTCCAAACCGCAG -3' (SEQ ID NO:02), where lower case letters indicate bases that add EcoRI and BamHI restriction sites for cloning) and a 7-kb downstream long-arm SalI fragment containing the ACAT2 stop codon and polyadenylation signal. This vector was used to generate targeted embryonic stem cells and mice (V. L. Meiner, et al., *Proc. Natl. Acad. Sci. USA* 93, 14041–14046 (1996)). The gene disruption was confirmed by Southern analysis of genomic DNA digested with Spel and a probe (primers: sense, 5'-CTGGCTGCCCACGCTGTGGTGCTC-3' (SEQ ID NO:03) and antisense, 5'-GACACAAAAGATCCCAGGCACAG3' (SEQ ID NO:04)) located upstream of the vector sequences. Subsequent genotyping in mice was done by PCR using primers A (5'-GTGTGCATCTGTCTCGATATGATG-3' (SEQ ID NO:05)), B (5'-GTCATGGACCACGACGTTCCAGGTG-3 (SEQ ID NO:06)') and C (5'-TACCGGTGGATGTGGAATGTGTGCG-3' (SEQ ID NO:07)). PCR conditions were 35 cycles of 94° C. for 1 min, 58° C. for 1 min, and 72° C. for 2 min. A and B amplify an 820-b fragment from the wild-type allele, and A and C amplify a 500-bp fragment from the targeted allele. Reverse transcriptase-PCR to demonstrate the absence of the C-terminal ACAT2 mRNA was performed using cDNA prepared from mouse liver and small intestine and primers (sense, (5'-GGCTGTACAGCTATGTGTATCAAG-3' (SEQ ID NO:08), and antisense, 5'-TTAGGGATGGCAGGACC-AAGA-3' (SEQ ID NO:09)) specific for the deleted coding sequences. RT-PCR of glyceraldehyde-3-phosphate dehydrogenase (G3PDH) was performed as a control to demonstrate cDNA integrity (R. V. Farese, Jr., et al., *J. Lipid Res.* 37, 347–360 (1996)). ACAT2$^{-/-}$ mice were viable and healthy, and offspring from heterozygous intercrosses were found in a Mendelian distribution. The ACAT2 gene disruption was confirmed by Southern analysis, and the absence of intact ACAT2 mRNA expression was demonstrated by RT-PCR of cDNA from mouse small intestine and liver.

Mice studied were of a mixed (50% C57BL/6J and 50% 129/SvJae) genetic background and were between 3–5 months of age. Mice were housed in a pathogen-free barrier facility (12-h light/12-h dark cycle) and fed either rodent chow (Picolab 20, Purina, Saint Louis, Mo.) or a synthetic high-fat, high-cholesterol (HF/HC) diet containing 7.5% (wt/wt) cocoa butter, 1.25% (wt/wt) cholesterol, and 0.5% (wt/wt) sodium cholate (Atherogenic Diet, ICN Biomedicals, Aurora, OH). For analysis of plasma, blood was obtained from the retroorbital plexus after mice were fasted for 4 h.

Data are presented as mean±SD. For parametric data, means were compared using t test, or analysis of variance followed by the Tukey test. For nonparametric data, the Mann-Whitney ranked sum test or Kruskal-Wallis test followed by the Tukey test was used.

The rate of incorporation of [$^{14}$C]oleoyl-CoA (Amersham) into cholesterol esters was assayed by the method of Erickson et al, *J. Lipid Res.* 21, 930–941 (1980), with modifications as described Cases, et al., *J. Biol. Chem.* 273, 26755–26764 (1998). Reactions were performed at 37° C. for 5 min with 100 μg of microsomal protein and 25 μM oleoyl-CoA (specific activity =18 μCi/μmol). Exogenous cholesterol (20 mol) was added to the microsomes as phosphatidylcholine:cholesterol (4:1 molar ratio) liposomes to measure apparent $V_{max}$ activities. ACAT activity in membranes was reduced by 92% in ACAT2$^{-/-}$ small intestine (5.1±2.5 vs. 61.9±58.7 pmol cholesterol ester formed/mg prot/min for wild-type mice, P<0.05) and by 99% in ACAT2$^{-/-}$ liver (8.8±5.2 vs. 575.3±208.9 pmol cholesterol ester formed/mg prot/min for wild-type mice, P<0.01) (FIG. lC). ACAT activity in adrenal glands, which express mainly ACAT1, was similar in wild-type and ACAT2$^{-/-}$ mice. There was no apparent upregulation of ACAT 1 activity in the small intestine or liver to compensate for ACAT2 deficiency. These results establish that ACAT2 is the major cholesterol esterification enzyme in mouse small intestine and liver.

Colorimetric assays were used to measure plasma lipids including total cholesterol (Spectrum kit, Abbott Diagnostics, Abbott Park, Ill.), free cholesterol (WAKO Chemicals, Neuss, Germany), triglycerides (Triglycerides/GB kit, Boehringer Mannhein, Indianapolis, Ind.), and phospholipids (Phospholipids B kit, WAKO Chemicals, Neuss, Germany). Analysis of lipids in lipoprotein fractions was performed after separating pooled mouse plasma samples (n=4) by fast-performance liquid chromatography (FPLC) using a Pharmacia Superose-6 column (Uppsala, Sweden) (Horie et al., *J. Biol Chem.* 267, 1962–1968 (1992). Fractions were assayed for total cholesterol, free cholesterol, phospholipids, and triglycerides (Triglycerides, Boehringer Mannhein, Indianapolis, Indiana, USA), and cholesterol esters were calculated by subtracting values of free cholesterol from total cholesterol. For tissue lipid measurements, mice were killed by cervical dislocation and exsanguinated. Lipids were extracted from tissues, and cholesterol ester and free cholesterol contents were measured by gas-liquid chromatography (Schwarz, et al., *J. Lipid Res.* 39, 1833–1843 (1998)). Tissue triglycerides were measured with a kit (Triglycerides 320A, Sigma, St. Louis, Mo.) as described in Jensen, et al., *Am. J. Physiol.* 273, R683–R689 (1997).

Plasma total cholesterol levels in chow-fed wild-type and ACAT2$^{-/-}$ mice were similar. When wild-type mice were fed a HF/HC diet, plasma cholesterol levels increased more than two-fold, whereas plasma triglyceride levels fell (from 32±7 to 18±7, P<0.05), presumably reflecting the replacement of triglycerides in the core of apoB-containing lipoproteins with cholesterol esters. In contrast, ACAT2$^{+/-}$ mice fed the HF/HC diet did not develop hypercholesterolemia (70±5 vs. 203±12 mg/dl for wild-type mice, P<0.01). In addition, their plasma triglyceride levels on the HF/HC diet (47±11 mg/dl) were similar to those in chow-fed mice and were more than twice those of wild-type mice fed this diet (P<0.01). Heterozygous ACAT2-deficient (ACAT2$^{-/-}$ mice fed the HF/HC diet had plasma total cholesterol levels that were intermediate between wild-type and ACAT2$^{-/-}$ mice (271±67 vs. 179±42 vs. 93±8 mg/dl for +/+, +/−, and −/−, respectively, in a separate analysis, P<0.05

Analysis of the lipid composition of lipoprotein subclasses showed that the increase in plasma total cholesterol in wild-type mice fed the HF/HC diet was primarily due to increased cholesterol esters in their apoB-containing lipoproteins [very low density lipoproteins (VLDL), intermediate density lipoproteins (IDL), and low density lipoproteins (LDL)]. Free cholesterol levels also increased in VLDL of wild-type mice fed this diet. In contrast, cholesterol esters and free cholesterol were not increased in these lipoproteins in ACAT2$^{-/-}$ mice fed the HF/HC diet. However, on both chow and HF/HC diets, ACAT2$^{-/-}$ mice had more triglycerides in VLDL, IDL, and LDL than wild-type mice. Other findings included higher free cholesterol levels in high density lipoproteins (HDL) of ACAT2$^{-/-}$ mice fed either diet, and higher phospholipid levels in VLDL and IDL of wild-type mice fed the HF/HC diet.

For immunoblotting, samples of pooled mouse plasma (n=4) were fractionated by FPLC using a Pharmacia Superose-6 column (Uppsala, Sweden). Fractions containing VLDL, IDL, and LDL were pooled, separated by 4% SDS-PAGE, transferred to nitrocellulose, incubated with a polyclonal antibody that recognizes the amino terminus of apolipoprotein (McCormick, et al., *J. Biol. Chem.* 271, 11963–1.1970 (1996)) (a gift from Steven Young, Gladstone Institute of Cardiovascular Disease), and binding of the antibodies was detected by enhanced chemiluminescence (Amersham).

Plasma levels of apoB, the primary structural apolipoprotein in VLDL, IDL, and LDL, were similar in lipoprotein fractions of chow-fed wild-type and ACAT2$^{-/-}$ mice (FIG. 2C); apoB100 levels were slightly greater than apoB48 levels, and both forms of apoB were highest in the LDL. When wild-type mice were fed the HF/HC diet, plasma apoB100 and apoB48 levels increased, and the ratio shifted towards more apoB48. In contrast, plasma apoB levels in ACAT2$^{-/-}$ mice fed the HF/HC diet were similar to those of chow-fed mice.

Because of the dramatic differences in the plasma lipoprotein response to HF/HC feeding, we examined the ultrastructural characteristics of the plasma lipoproteins (d<1.063 gm/ml, which includes VLDL, IDL, and LDL) from wild-type and ACAT2$^{-/-}$ mice (Non-HDL lipoproteins (d<1.063) were isolated from pooled mouse plasma (n=4) by ultracentrifugation, and samples were examined by electron microscopy after negative staining (Hamilton, Jr. et al., *J. Lipid Res.* 21, 981–992 (1980))). In wild-type mice fed the HF/HC diet, the lipoproteins were characterized by large numbers of particles of typical VLDL diameters (~30–80 nm). Many particles exhibited a flattened surface, characteristic of cholesterol-ester rich lipoproteins. In contrast, the majority of lipoproteins in ACAT2$^{-/-}$ mice fed the HF/HC diet were smaller )~16–18 nm) and exhibited an electron-lucent core, characteristic of triglyceride-rich lipoproteins. Particularly striking was the virtual absence of VLDL-sized particles (>28 nm) in HF/HC-fed ACAT2$^{-/-}$) plasma. In wild-type and ACAT2$^{-/-}$ mice fed a chow diet, the morphology and diameters of the lipoproteins were similar.

The HF/HC diet contains cholic acid and promotes cholelithiasis in susceptible strains of mice (DW G751). When wild-type male mice were fed this diet for 3–6 weeks, 7 of 7 developed gallstones. In contrast, none of the ACAT2$^{-/-}$ mice (9 of 9) developed gallstones. When the HF/HC diet was fed for more than 3 months, nearly all wild-type mice developed gallstones, whereas gallstones were rare in ACAT2$^{-/-}$ mice (Table 1). Gallstone formation was intermediate in ACAT2$^{+/-}$ mice.

Table 1. Resistance to Gallstone Formation in ACAT2$^{-/-}$ mice

Semi-quantitative analysis of gallstone formation in wild type and ACAT2$^{-/-}$ mice fed a lithogenic diet for more than 3 months. Gallstone formation was visually scored and assigned values of high (full of large stones), medium (~half-full), low (few stones), or none.

| ACAT2 Genotype | Gallstones | | | |
| --- | --- | --- | --- | --- |
| | High | Medium | Low | None |
| +/+ | 8 | 2 | 3 | 1 |
| +/− | 0 | 9 | 1 | 0 |
| −/− | 0 | 0 | 3 | 11 |

We hypothesized that the protection from diet-induced hypercholesterolemia and gallstone formation in ACAT2$^{-/-}$ mice resulted from a block in their ability to absorb dietary cholesterol. In chow-fed mice, cholesterol absorption, as measured by a radiolabeled tracer (Cholesterol absorption was measured by a fecal isotope ratio method using [4-$^4$C] cholesterol (Amersham) and [5,6-$^3$H]sitostanol (American Radiolabeled Chemicals, Inc., St. Louis, Mo.) as described in Schwarz, et al., *J. Lipid Res.* 39, 1833–1843 (1998) and Turley, et al., *Gastroenterology* 107, 444–452 (1994) Non-fasted mice were dosed with [$^{14}$C]cholesterol and [$^3$H] sitostanol in medium chain-length triacylglycerol oil. Feces were collected for 24 h after dosing, and the ratio of $^{14}$C to $^3$H in aliquots of samples was used to calculate the percent cholesterol absorption. For chow-fed mice, 0.67 $\mu$Ci of [$^{14}$C]cholesterol and 1.67 $\mu$Ci of [$^3$H]sitostanol were used; for mice fed the HF/HC diet, the amounts of tracers were increased ten-fold.), was similar in wild-type and ACAT2$^{-/-}$ mice. In mice fed the HF/HC diet, however, cholesterol absorption was seven-fold lower in ACAT2$^{-/-}$ mice than in wild-type mice ( 10.3±3.9% vs. 1.4±0.5%, P<0.01)( On this diet, the absorption of the tracer was reduced in both groups of mice as compared with chow-fed mice. This occurred due to dilution of the tracer by the large pool of unlabeled cholesterol supplied by the HF/HC diet. The mass of cholesterol absorbed normally increases with cholesterol feeding, despite the decrease in tracer absorption (ES 10194)).

We hypothesized that the capacity to increase dietary cholesterol uptake was reduced in ACAT2$^{-/-}$ mice, most likely due to a reduced ability to synthesize cholesterol esters for intestinal lipoprotein synthesis and secretion. We reasoned that a difference in cholesterol absorption capacity would be reflected in hepatic cholesterol accumulation in mice fed the HF/HC diet. When fed this diet, wild-type mice developed fatty livers (Tissues were fixed by perfusion in 4% paraformaldehyde in phosphate buffered saline (pH 7.3). Tissues were removed and immersed in 2% osmium tetroxide in 0.1M sodium phosphate buffer, pH 7.4, to stain neutral lipids. Tissues were then dehydrated in an ethanol series, transitioned into propylene oxide and embedded in Epon resin. Sections (1 $\mu$m) were cut with a glass knife and stained in warm toluidine blue.) due to a large accumulation of cholesterol esters, whereas ACAT2$^{-/-}$ mice had normal appearing livers with a virtual absence of cholesterol esters in their livers. Free cholesterol levels were also not increased in livers of ACAT2$^{-/-}$ mice. Hepatic triglyceride concentrations were similar in wild-type and ACAT2$^{-/-}$ mice fed the chow diet [15.4±5.5 and 11.9±3.4 $\mu$g/mg tissue for wild-type and ACAT2$^{-/-}$ mice (n=3 each)], but were lower in ACAT2$^{-/-}$ mice fed the HF/HC diet [7.9±0.5 vs. 10.9±0.9 $\mu$g/mg tissue for wild-type mice (n=3 each), P<0.01].

To further test the hypothesis that a reduced capacity for cholesterol absorption in ACAT2$^{-/-}$ mice was effectively "shielding" the liver from cholesterol provided by the FF/HC diet, we examined the expression of several key genes involved in hepatic cholesterol metabolism. Mice in the fed state (three hours after the onset of the dark cycle) were killed by cervical dislocation, and liver samples were removed. Total RNA was extracted from tissue using Trizol (Life Technologies) and samples were pooled (n=3) for analysis. Northern analysis was performed with total RNA samples (15 $\mu$g) that were separated by electrophoresis in 1% agarose-formaldehyde gels, transferred to nylon membranes, and hybridized with $^{32}$P-labeled probes for 3-hydroxy-3-methyl glutaryl coenzymeA reductase (HMGR) [a gift from Jay Horton, University of Texas-Southwestern Medical Center (UTSWMC)], low density lipoprotein receptor (LDLR) (a gift from Joachim Herz, UTSWMC), and cholesterol $\alpha$-hydroxylase (Cyp7A) (a gift from David Russell,UTSWMC). Membranes were re-probed for glyceraldehyde-3-phosphate dehydrogenase (G3PDH) to normalize for differences in loading, and signal quantification was performed using a phosphoimager (BioRad Molecular Imager FX, Hercules, Calif.) and quantitation software (BioRad Quantity One). On the chow diet, the expression levels of HMG CoA reductase and LDL receptor were similar in wild-type and ACAT2$^{-/-}$ mice. On the HF/HC diet, the expression of these genes was reduced in wild-type mice, reflecting the accumulation of cholesterol in the liver. In contrast, the expression of these genes in ACAT2$^{-/-}$ mice fed the HF/HC diet was similar to levels in chow-fed mice, consistent with the lack of cholesterol accumulation in ACAT2$^{-/-}$ livers. Expression levels of cholesterol 7$\alpha$-hydroxylase, a key enzyme involved in bile acid synthesis, were similar in wild-type and ACAT2$^{-/-}$ mice fed a chow diet and were suppressed in both groups of mice fed the HF/HC diet (not shown).

The block in cholesterol esterification in ACAT2$^{-/-}$ enterocytes might be expected to cause marked elevations in cellular free cholesterol levels in response to the HF/HC diet. However, free cholesterol levels were increased by only 30% in the small intestine of ACAT2$^{-/-}$ mice, and intestinal enterocytes appeared normal in histologic sections (not shown). We hypothesized that upregulation of ABC1, a recently identified mediator of cellular cholesterol efflux (AB336, MB347, SR352), might function to excrete the free cholesterol back into the intestinal lumen.

Our studies show that ACAT2 plays a major role in mouse cholesterol metabolism. ACAT2 deficiency caused a dramatic, near-total depletion of cholesterol esters from the apoB-containing lipoproteins. Instead these lipoproteins contained mostly triglycerides in their cores. This occurred when ACAT2$^{-/-}$ mice were fed either a chow diet or a HF/JHC diet. This result establishes that ACAT2 plays a crucial role in synthesizing cholesterol esters for lipoprotein synthesis and secretion in mice. Our findings indicate that apoB-containing lipoproteins can be synthesized despite the virtual absence of cholesterol esters, addressing a long-standing debate about whether cholesterol ester synthesis is required for the synthesis and secretion of apoB-containing lipoproteins (JD1667). However, normal cholesterol ester availability may be needed to synthesize and assemble larger particles (i.e., >28 nm). Our results also address the hypothesis that ACAT1 is functionally linked to the synthesis of cholesterol esters for storage in cytosolic droplets, whereas ACAT2 is functionally coupled to the synthesis of cholesterol esters for lipoprotein secretion. Our results indicate that this is an oversimplification, as ACAT2 is the predominant ACAT in mouse liver and was capable of synthesizing cholesterol esters for storage in in HF/HC-fed wild-type mice.

ACAT2$^{-/-}$ mice did not become hypercholesterolemic when challenged with a diet containing high levels of fat and cholesterol, implicating ACAT2 as a major determinant of responsiveness to dietary cholesterol in mice. Of note, a quantitative trait locus (QTL) for the response of plasma VLDL- and LDL-cholesterol to HF/HC feeding has been mapped to a region of mouse chromosome 15 containing the ACAT2 gene. Because the phenotype of this quantitative trait and ACAT2-deficiency are similar, ACAT2 may be the responsible gene. Supporting this hypothesis, ACAT2$^{+/-}$ mice that were fed the HF/HC diet had plasma total cholesterol levels that were intermediate between wild-type and ACAT2$^{-/-}$ mice. It should be noted, however, that the HF/HC diet employed in these studies is formulated to maximize cholesterol absorption. Therefore, the importance of ACAT2 in regulating the plasma cholesterol response at lower dietary cholesterol levels remains to be determined.

ACAT2 deficiency dramatically reduced gallstone formation in response to feeding the HF/HC diet, which contains cholic acid and promotes lithogenesis in mice (DW G75 1). Moreover, our results indicate that the gallstone resistance may be a quantitative trait, as gallstone formation was intermediate in ACAT2$^{+/-}$ mice. From QTL analyses in mice, seven regions on different chromosomes have been identified to contain loci (Lith genes) that confer susceptibility to gallstone formation (BK7729, FL224). Our results identify ACAT2, which does not map to a previously identified locus, as an additional Lith gene. The previous QTL analyses might not have identified ACAT2 as a susceptibility locus if the mouse strains analyzed did not differ substantially in ACAT2 expression. The decrease in gallstone formation in ACAT2$^{-/-}$ mice contrasts with studies that have associated decreased hepatic ACAT activity with increased gallstone formation (Smith, et. al., *J. Lipid Res.* 31, 1993–2000 (1990)). These studies have hypothesized that decreased hepatic ACAT activity results in increased free cholesterol excretion and lithogenicity in the bile. However, our results indicate that ACAT2$^{-/-}$ mice were resistant to gallstones due to the loss of ACAT activity in the intestine, which shielded the liver from the dietary cholesterol. ACAT2's role as a determinant of responsiveness to dietary cholesterol appears to result in part from its role in intestinal cholesterol absorption. Although ACAT2 was not required for cholesterol absorption when dietary cholesterol was low, ACAT2 deficiency limited the ability to increase cholesterol absorption capacity when dietary cholesterol was high. These results can be interpreted in light of the previous finding that intestinal cholesterol absorption requires intact chylomicron synthesis and secretion. This indicates that when dietary cholesterol is low, ACAT2$^{-/-}$ mice can incorporate absorbed cholesterol into nascent chylomicrons as free cholesterol molecules at the surface of particles. However, when dietary cholesterol is increased, ACAT2$^{-/-}$ enterocytes are unable to synthesize cholesterol esters that would normally be added to the cores of nascent chylomicrons. As a result, the capacity to increase the mass of cholesterol absorbed is limited. Thus, intestinal ACAT activity may not be required for cholesterol absorption per se, but is necessary to increase the capacity for cholesterol absorption in response to high levels of dietary cholesterol. These results help to clarify the long-standing debate on the role of ACAT in cholesterol absorption. Our results also are consistent with a number of studies in animals in which ACAT inhibitors were most effective in reducing cholesterol absorption in cholesterol-fed animals (BD19) (Recently increased biliary cholesterol excretion was proposed as a mechanism that can reduce dietary cholesterol absorption (ES10194). (Although this mechanism probably accounts for the decrease in tracer absorption in mice fed the HF/HC diet in our study, it is unlikely to explain the lower cholesterol absorption in ACAT2$^{-/-}$ mice fed this diet).

Recently, we showed that hypercholesterolemic mice lacking ACAT1 unexpectedly developed massive deposition of free cholesterol in skin and brain and lacked protection from atherosclerosis development (MA711). Although the latter findings occurred in the extreme case of severe hyperlipidemia and total ACAT1 deficency, these findings and the current results indicate that specific inhibitors that target ACAT2 rather than ACAT1 find use in the treatment of a variety of disease conditions.

In sum, the above results show that mice lacking ACAT2 are deficient in ACAT activity in the small intestine and liver and are protected from diet-induced hypercholesterolemia and gallstone formation. The contributing mechanisms include an inability to incorporate cholesterol esters into intestinal- and hepatic-derived lipoproteins and a decreased capacity to absorb dietary cholesterol. These results indicate that ACAT2 plays an important role in the response to dietary cholesterol and that selective ACAT2 inhibition is useful for preventing diet-induced hypercholesterolemia and gallstones, as well as reducing plasma cholesterol levels.

It is apparent from the above results and discussion that polynucleotides encoding novel mammalian ACAT-2 enzymes, as well as the novel polypeptides encoded thereby, are provided. The subject invention is important for both research and therapeutic applications. Using the ACAT-2 probes of the subject invention, the role of ACAT-2 and its regulation in a number of physiological processes can be studied in vivo. The subject invention also provides for important new ways of treating diseases associated with ACAT-2 activity.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of modulating the activity of Acyl COA:Cholesterol Acyltransferase-2 (ACAT-2) in vivo in a host, said method comprising:

administering to said host, an effective amount of an agent that modulates the activity of said ACAT-2, wherein said ACAT-2 has at least about 80% amino acid identity to SEQ ID NO:12 or SEQ ID NO:13.

2. The method according to claim 1, wherein said modulating is inhibiting.

3. A method of modulating the activity of Acyl COA:Cholesterol Acyltransferase-2 (ACAT-2) in vitro, said method comprising:

contacting said ACAT-2 with an agent that modulates the activity of said ACAT-2, wherein said ACAT-2 has at least about 80% amino acid identity to SEQ ID NO:12 or SEQ ID NO:13.

4. The method according to claim 3, wherein said modulating is inhibiting.

5. The method according to claim 4, wherein the agent is an antisense molecule.

6. The method according to claim 1, wherein said agent is an antisense molecule.

* * * * *

```
                              SEQUENCE LISTING

<160> NUMBER OF SEQ ID NOS: 17

<210> SEQ ID NO 1
<211> LENGTH: 33
<212> TYPE: DNA
<213> ORGANISM: Artificial Sequence
<220> FEATURE:
<223> OTHER INFORMATION: primer

<400> SEQUENCE: 1
cgcggatccg gctctgctgc tctccatctt gca                                 33

<210> SEQ ID NO 2
<211> LENGTH: 33
<212> TYPE: DNA
<213> ORGANISM: Artificial Sequence
<220> FEATURE:
<223> OTHER INFORMATION: primer

<400> SEQUENCE: 2
cgcggatccg aacatcctgt ctccaaaccg cag                                 33

<210> SEQ ID NO 3
<211> LENGTH: 24
<212> TYPE: DNA
<213> ORGANISM: Artificial Sequence
<220> FEATURE:
<223> OTHER INFORMATION: primer

<400> SEQUENCE: 3
ctggctgccc acgctgtggt gctc                                           24

<210> SEQ ID NO 4
<211> LENGTH: 23
<212> TYPE: DNA
<213> ORGANISM: Artificial Sequence
<220> FEATURE:
<223> OTHER INFORMATION: primer

<400> SEQUENCE: 4
gacacaaaag atcccaggca cag                                            23

<210> SEQ ID NO 5
<211> LENGTH: 24
<212> TYPE: DNA
<213> ORGANISM: Artificial Sequence
<220> FEATURE:
<223> OTHER INFORMATION: primer

<400> SEQUENCE: 5
gtgtgcatct gtctcgatat gatg                                           24

<210> SEQ ID NO 6
<211> LENGTH: 25
<212> TYPE: DNA
```

<213> ORGANISM: Artificial Sequence
<220> FEATURE:
<223> OTHER INFORMATION: primer

<400> SEQUENCE: 6
gtcatggacc acgacgttcc aggtg                                    25

<210> SEQ ID NO 7
<211> LENGTH: 25
<212> TYPE: DNA
<213> ORGANISM: Artificial Sequence
<220> FEATURE:
<223> OTHER INFORMATION: primer

<400> SEQUENCE: 7
gtcatggacc acgacgttcc aggtg                                    25

<210> SEQ ID NO 8
<211> LENGTH: 24
<212> TYPE: DNA
<213> ORGANISM: Artificial Sequence
<220> FEATURE:
<223> OTHER INFORMATION: primer

<400> SEQUENCE: 8
ggctgtacag ctatgtgtat caag                                     24

<210> SEQ ID NO 9
<211> LENGTH: 21
<212> TYPE: DNA
<213> ORGANISM: Artificial Sequence
<220> FEATURE:
<223> OTHER INFORMATION: primer

<400> SEQUENCE: 9
ttagggatgg caggaccaag a                                        21

<210> SEQ ID NO 10
<211> LENGTH: 1607
<212> TYPE: DNA
<213> ORGANISM: mouse
<220> FEATURE:
<221> NAME/KEY: misc_feature
<222> LOCATION: (176)...(176)
<223> OTHER INFORMATION: N = a, g, c or t

<400> SEQUENCE: 10
ctgtgtgctg tccgctctac actggcacca tgcagccaaa ggtgcccag cttcggagga      60 gagaagggct gggagaggag caggagaagg agcccgtgg aggagaaggg aacgcaagga     120
cacacggaac cccagacttg gtgcaatgga ctcgacatat ggaggctgtg aagacncagt    180
ttctggagca agcacagaga gagttggcag agctgttgga tcgggcccta tgggaggcta    240
tgcaagctta cccaaacaa gacagacctc ttccctccgc tgcccagat tctacaagca     300 agaccccgga gttacgccct ggaaaacgga agttttcgt cgcccgcaag tcactgatcg    360
atgagctaat ggaggtgcaa catttccgaa ccatctacca catgttcata gcgggcctat    420
ggttcttgat catcagcacc ctggccatcg acttcattga tgagggcagg ttgatgctgg    480
agtttgactt actcctcttc agcttcggac agctgccctt ggcgctgatg acctgggttc    540
ccatgttcct gtatacgctc ctagtgccct accagaccct gtggctgtgg gccaggccgc    600
gcgctggggg tgcctggatg ctgggggcca gctgggctg cgttctgctg ctgcccacg     660 ctgtggtgct ctgcgtcctg ccggtgcacg tgtcagtgag gcatgagctt ccgcccgcct    720

-continued

```
cgcgctgcgt gctggtctتt gagcaggtca gattgctgat gaaaagctac tccttcctga        780
gagagactgt gcctgggatc ttttgtgtca gacgaggaaa gggcatcagc cccccaagtt        840
tctccagcta cctctacttc ctcttctgcc ctacacttat ctacagagag acatacccca        900
ggacacccag catcaggtgg aactatgtgg ccaagaactt tgcccaggtc ctgggctgtt        960
tgctctatgc ctgcttcatc ctgggccgcc tctgtgtccc tgtctttgcc aacatgagcc       1020
gggaaccctt cagcacccgg gctctgctgc tctccatctt gcatgccacg gggccaggca       1080
tcttcatgct gctcctcatc ttcttcgcct cctgcactg ctggctcaac gccttcgccg        1140
agatgctgcg gtttggagac aggatgttct accgggactg gtggaactcg acttccttct       1200
ccaactacta ccgcacctgg aacgtcgtgg tccatgactg gctgtacagc tatgtgtatc       1260
aagatgggct gtggctctta ggcaggcggg ctcgcggggt ggccatgctg ggagtgttcc       1320
tggtgtctgc ggtggttcat gagtatatct tctgcttcgt cctggggttc ttctacccgg       1380
tcatgctgat gctattcctt gttttcgggg gctgctgaa tttcaccatg aacgacaggc        1440
acacaggtcc agcctggaac atcctgatgt ggacctttct cttcatgggc cagggcatcc       1500
aggtcagcct atactgccag gagtggtatg ctcgtcgaca ctgtcccctg ccccagacaa       1560
cattctgggg gatggtgaca ccccaatctt ggtcctgcca tacctag                    1607
```

<210> SEQ ID NO 11
<211> LENGTH: 1509
<212> TYPE: DNA
<213> ORGANISM: human
<220> FEATURE:
<221> NAME/KEY: misc_feature
<222> LOCATION: (571)...(571)
<223> OTHER INFORMATION: N = a, g, c or t
<220> FEATURE:
<221> NAME/KEY: misc_feature
<222> LOCATION: (573)...(573)
<223> OTHER INFORMATION: N = a, g, c or t

<400> SEQUENCE: 11

```
atggagccag gcggggcccg tctgcgtctg cagaggacag aagggctggg aggggagcgg         60
gagcgccaac cctgtggaga tggaaacact gagacgcaca gagccccgga cttggtacaa        120
tggacccgac acatggaggc tgtgaaggca caattgctgg agcaagcgca gggacaactg        180
agggagctgc tggatcgggc catgcgggag gctatacaat cctacccatc acaagacaaa        240
cctctgcccc cacctccccc aggttccttg agcagtgagc tgatggaggt gcagcatttc        300
cgcaccatct accacatgtt catcgctggc ctgtgtgtct tcatcatcag caccctggcc        360
atcgacttca ttgatgaggg caggctgctg ctggagtttg acccactgat cttcagcttc        420
ggacagctgc cattggcgct ggtgacctgg gtgcccatgt ttctgtccac cctgttggcg        480
ccgtaccagg cctacggct gtgggccagg gcacctgga cgcaggcgac gggcctaggc        540
tgtgcgctgc tagccgccca cgccgtggtg ntntgcgcgc tgccggtcca cgtggccgtg        600
gagcatcagc tcccgccggc ctcccgttgt gtcctggtct cgagcaggt taggttcctg        660 atgaaaagct actccttcct gagagaggct gtgcctggga cccttcgtgc cagacgaggt        720 gagggggatcc aggcccccag tttctccagc tacctctact tcctcttctg cccaacactc        780
atctacaggg agacttaccc taggacgccc tatgtcaggt ggaattatgt ggccaagaac        840
tttgcccagg ccctgggatg tgtgctctat gcctgcttca tcctgggccg cctctgtgtt        900
cctgtctttg ccaacatgag ccgagacccc ttcagcaccc gtgccctggt gctctctatc        960
```

```
ctgcatgcca cgttgccagg catcttcatg ctgctgctca tcttctttgc cttcctccat    1020
tgctggctca acgcctttgc cgagatgcta cgatttggag acaggatgtt ctaccgggac    1080
tggtggaact caacgtcctt ctccaactac taccgcactt ggaacgtggt ggtccatgac    1140
tggctgtaca gctacgtgta tcaggatggg ctgcggctcc ttggtgcccg ggcccgaggg    1200
gtagccatgc tgggtgtgtt cctggtctcc gcagtggccc atgagtatat cttctgcttc    1260
gtcctggggt tcttctatcc cgtcatgctg atactcttcc ttgtcattgg aggaatgttg    1320
aacttcatga tgcatgacca gcgcaccggc ccggcatgga acgtgctgat gtggaccatg    1380
ctgtttctag gccagggaat ccaggtcggc ctgtactgcc aggagtggta cgcacggcgg    1440
cactgcccct accccaggc aactttctgg gggctggtga cacctcgatc ttggtcctgc    1500 cataccta g                                                           1509
```

<210> SEQ ID NO 12
<211> LENGTH: 525
<212> TYPE: PRT
<213> ORGANISM: mouse

<400> SEQUENCE: 12

```
Met Gln Pro Lys Val Pro Gln Leu Arg Arg Arg Glu Gly Leu Gly Glu
1               5                   10                  15

Glu Gln Glu Lys Gly Ala Arg Gly Gly Glu Gly Asn Ala Arg Thr His
            20                  25                  30

Gly Thr Pro Asp Leu Val Gln Trp Thr Arg His Met Glu Ala Val Lys
        35                  40                  45

Thr Gln Phe Leu Glu Gln Ala Gln Arg Glu Leu Ala Glu Leu Leu Asp
    50                  55                  60

Arg Ala Leu Trp Glu Ala Met Gln Ala Tyr Pro Lys Gln Asp Arg Pro
65                  70                  75                  80

Leu Pro Ser Ala Ala Pro Asp Ser Thr Ser Lys Thr Pro Glu Leu Arg
                85                  90                  95

Pro Gly Lys Arg Lys Val Phe Val Ala Arg Lys Ser Leu Ile Asp Glu
            100                 105                 110

Leu Met Glu Val Gln His Phe Arg Thr Ile Tyr His Met Phe Ile Ala
        115                 120                 125

Gly Leu Trp Phe Leu Ile Ile Ser Thr Leu Ala Ile Asp Phe Ile Asp
    130                 135                 140

Glu Gly Arg Leu Met Leu Glu Phe Asp Leu Leu Leu Phe Ser Phe Gly
145                 150                 155                 160

Gln Leu Pro Leu Ala Leu Met Thr Trp Val Pro Met Phe Leu Tyr Thr
                165                 170                 175

Leu Leu Val Pro Tyr Gln Thr Leu Trp Leu Trp Ala Arg Pro Arg Ala
            180                 185                 190

Gly Gly Ala Trp Met Leu Gly Ala Ser Leu Gly Cys Val Leu Leu Ala
        195                 200                 205

Ala His Ala Val Val Leu Cys Val Leu Pro Val His Val Ser Val Arg
    210                 215                 220

His Glu Leu Pro Pro Ala Ser Arg Cys Val Leu Val Phe Glu Gln Val
225                 230                 235                 240

Arg Leu Leu Met Lys Ser Tyr Ser Phe Leu Arg Glu Thr Val Pro Gly
                245                 250                 255

Ile Phe Cys Val Arg Arg Gly Lys Gly Ile Ser Pro Pro Ser Phe Ser
            260                 265                 270
```

```
Ser Tyr Leu Tyr Phe Leu Phe Cys Pro Thr Leu Ile Tyr Arg Glu Thr
        275                 280                 285

Tyr Pro Arg Thr Pro Ser Ile Arg Trp Asn Tyr Val Ala Lys Asn Phe
        290                 295                 300

Ala Gln Val Leu Gly Cys Leu Leu Tyr Ala Cys Phe Ile Leu Gly Arg
305                 310                 315                 320

Leu Cys Val Pro Val Phe Ala Asn Met Ser Arg Glu Pro Phe Ser Thr
                325                 330                 335

Arg Ala Leu Leu Leu Ser Ile Leu His Ala Thr Gly Pro Gly Ile Phe
            340                 345                 350

Met Leu Leu Leu Ile Phe Phe Ala Phe Leu His Cys Trp Leu Asn Ala
        355                 360                 365

Phe Ala Glu Met Leu Arg Phe Gly Asp Arg Met Phe Tyr Arg Asp Trp
    370                 375                 380

Trp Asn Ser Thr Ser Phe Ser Asn Tyr Tyr Arg Thr Trp Asn Val Val
385                 390                 395                 400

Val His Asp Trp Leu Tyr Ser Tyr Val Tyr Gln Asp Gly Leu Trp Leu
                405                 410                 415

Leu Gly Arg Arg Ala Arg Gly Val Ala Met Leu Gly Val Phe Leu Val
            420                 425                 430

Ser Ala Val His Glu Tyr Ile Phe Cys Phe Val Leu Gly Phe Phe
        435                 440                 445

Tyr Pro Val Met Leu Met Leu Phe Leu Val Phe Gly Leu Leu Asn
    450                 455                 460

Phe Thr Met Asn Asp Arg His Thr Gly Pro Ala Trp Asn Ile Leu Met
465                 470                 475                 480

Trp Thr Phe Leu Phe Met Gly Gln Gly Ile Gln Val Ser Leu Tyr Cys
                485                 490                 495

Gln Glu Trp Tyr Ala Arg Arg His Cys Pro Leu Pro Gln Thr Thr Phe
            500                 505                 510

Trp Gly Met Val Thr Pro Gln Ser Trp Ser Cys His Thr
        515                 520                 525

<210> SEQ ID NO 13
<211> LENGTH: 502
<212> TYPE: PRT
<213> ORGANISM: human
<220> FEATURE:
<221> NAME/KEY: UNSURE
<222> LOCATION: (191)...(191)
<223> OTHER INFORMATION: Xaa = any amino acid

<400> SEQUENCE: 13

Met Glu Pro Gly Gly Ala Arg Leu Arg Leu Gln Arg Thr Glu Gly Leu
1               5                   10                  15

Gly Gly Glu Arg Glu Arg Gln Pro Cys Gly Asp Gly Asn Thr Glu Thr
            20                  25                  30

His Arg Ala Pro Asp Leu Val Gln Trp Thr Arg His Met Glu Ala Val
        35                  40                  45

Lys Ala Gln Leu Leu Glu Gln Ala Gln Gly Gln Leu Arg Glu Leu Leu
    50                  55                  60

Asp Arg Ala Met Arg Glu Ala Ile Gln Ser Tyr Pro Ser Gln Asp Lys
65                  70                  75                  80

Pro Leu Pro Pro Pro Pro Gly Ser Leu Ser Ser Glu Leu Met Glu
                85                  90                  95

Val Gln His Phe Arg Thr Ile Tyr His Met Phe Ile Ala Gly Leu Cys
```

-continued

```
                100                 105                 110
Val Phe Ile Ile Ser Thr Leu Ala Ile Asp Phe Ile Asp Glu Gly Arg
            115                 120                 125
Leu Leu Leu Glu Phe Asp Pro Leu Ile Phe Ser Phe Gly Gln Leu Pro
130                 135                 140
Leu Ala Leu Val Thr Trp Val Pro Met Phe Leu Ser Thr Leu Leu Ala
145                 150                 155                 160
Pro Tyr Gln Ala Leu Arg Leu Trp Ala Arg Gly Thr Trp Thr Gln Ala
                165                 170                 175
Thr Gly Leu Gly Cys Ala Leu Leu Ala Ala His Ala Val Val Xaa Cys
            180                 185                 190
Ala Leu Pro Val His Val Ala Val Glu His Gln Leu Pro Pro Ala Ser
            195                 200                 205
Arg Cys Val Leu Val Phe Glu Gln Val Arg Phe Leu Met Lys Ser Tyr
            210                 215                 220
Ser Phe Leu Arg Glu Ala Val Pro Gly Thr Leu Arg Ala Arg Arg Gly
225                 230                 235                 240
Glu Gly Ile Gln Ala Pro Ser Phe Ser Ser Tyr Leu Tyr Phe Leu Phe
                245                 250                 255
Cys Pro Thr Leu Ile Tyr Arg Glu Thr Tyr Pro Arg Thr Pro Tyr Val
            260                 265                 270
Arg Trp Asn Tyr Val Ala Lys Asn Phe Ala Gln Ala Leu Gly Cys Val
            275                 280                 285
Leu Tyr Ala Cys Phe Ile Leu Gly Arg Leu Cys Val Pro Val Phe Ala
            290                 295                 300
Asn Met Ser Arg Asp Pro Phe Ser Thr Arg Ala Leu Val Leu Ser Ile
305                 310                 315                 320
Leu His Ala Thr Leu Pro Gly Ile Phe Met Leu Leu Ile Phe Phe
                325                 330                 335
Ala Phe Leu His Cys Trp Leu Asn Ala Phe Ala Glu Met Leu Arg Phe
            340                 345                 350
Gly Asp Arg Met Phe Tyr Arg Asp Trp Trp Asn Ser Thr Ser Phe Ser
            355                 360                 365
Asn Tyr Tyr Arg Thr Trp Asn Val Val His Asp Trp Leu Tyr Ser
370                 375                 380
Tyr Val Tyr Gln Asp Gly Leu Arg Leu Leu Gly Ala Arg Ala Arg Gly
385                 390                 395                 400
Val Ala Met Leu Gly Val Phe Leu Val Ser Ala Val Ala His Glu Tyr
                405                 410                 415
Ile Phe Cys Phe Val Leu Gly Phe Phe Tyr Pro Val Met Leu Ile Leu
            420                 425                 430
Phe Leu Val Ile Gly Gly Met Leu Asn Phe Met Met His Asp Gln Arg
            435                 440                 445
Thr Gly Pro Ala Trp Asn Val Leu Met Trp Thr Met Leu Phe Leu Gly
            450                 455                 460
Gln Gly Ile Gln Val Gly Leu Tyr Cys Gln Glu Trp Tyr Ala Arg Arg
465                 470                 475                 480
His Cys Pro Leu Pro Gln Ala Thr Phe Trp Gly Leu Val Thr Pro Arg
                485                 490                 495
Ser Trp Ser Cys His Thr
            500
```

<210> SEQ ID NO 14

```
<211> LENGTH: 24
<212> TYPE: DNA
<213> ORGANISM: Artificial Sequence
<220> FEATURE:
<223> OTHER INFORMATION: primer

<400> SEQUENCE: 14
actgtgcctg ggatcttttg tgtc                                              24

<210> SEQ ID NO 15
<211> LENGTH: 26
<212> TYPE: DNA
<213> ORGANISM: Artificial Sequence
<220> FEATURE:
<223> OTHER INFORMATION: primer

<400> SEQUENCE: 15
ctcgcggggt ggccatgctg ggagtg                                            26

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
tcttctatcc cgtcatgctg                                                   20

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
ggtccacatc agcacgttcc                                                   20
```